(12) United States Patent
Wei et al.

(10) Patent No.: US 7,915,217 B2
(45) Date of Patent: Mar. 29, 2011

(54) TREATMENT OF FRUITS OR VEGETABLES WITH HYPERSENSITIVE RESPONSE ELICITOR TO INHIBIT POSTHARVEST DISEASE OR DESICCATION

(75) Inventors: Zhong-Min Wei, Kirkland, WA (US); Dewen Qiu, Seattle, WA (US); Dean Remick, Lake Placid, FL (US)

(73) Assignee: Plant Health Care, Inc., Pittsburgh, PA (US)

(*) Notice: Subject to any disclaimer, the term of this patent is extended or adjusted under 35 U.S.C. 154(b) by 0 days.

(21) Appl. No.: 10/847,142

(22) Filed: May 17, 2004

(65) Prior Publication Data

US 2004/0265442 A1 Dec. 30, 2004

Related U.S. Application Data

(63) Continuation of application No. 09/835,684, filed on Apr. 16, 2001, now abandoned.

(60) Provisional application No. 60/198,359, filed on Apr. 19, 2000.

(51) Int. Cl.
*C07K 14/27* (2006.01)
*C07K 14/195* (2006.01)
*C12N 15/82* (2006.01)

(52) U.S. Cl. ........... 514/2; 435/69.1; 435/419; 435/849; 800/279; 800/288

(58) Field of Classification Search .................. 435/847; 514/2; 424/93
See application file for complete search history.

(56) References Cited

U.S. PATENT DOCUMENTS

| | | | |
|---|---|---|---|
| 5,708,139 A | 1/1998 | Collmer et al. | |
| 5,776,889 A * | 7/1998 | Wei et al. ........................ | 514/2 |
| 5,849,868 A | 12/1998 | Beer et al. | |
| 5,850,015 A | 12/1998 | Bauer et al. | |
| 5,858,786 A | 1/1999 | Collmer et al. | |
| 5,859,324 A | 1/1999 | Wei et al. | |
| 5,859,332 A | 1/1999 | Strittmatter et al. | |
| 5,977,060 A | 11/1999 | Zitter et al. | |
| 6,001,959 A | 12/1999 | Bauer et al. | |
| 6,172,184 B1 | 1/2001 | Collmer et al. | |
| 6,174,717 B1 | 1/2001 | Beer et al. | |
| 6,228,644 B1 | 5/2001 | Bogdanove et al. | |
| 6,235,974 B1 | 5/2001 | Qiu et al. | |
| 6,262,018 B1 | 7/2001 | Kim et al. | |
| 6,277,814 B1 | 8/2001 | Qiu et al. | |

FOREIGN PATENT DOCUMENTS

| | | |
|---|---|---|
| WO | WO 98/54214 | 12/1998 |
| WO | WO 00/02996 | 1/1999 |
| WO | WO 99/07207 | 2/1999 |
| WO | WO 99/07208 | 2/1999 |
| WO | WO 99/11133 | 3/1999 |
| WO | WO 00/20452 | 4/2000 |
| WO | WO 00/20616 | 4/2000 |
| WO | WO 00/28055 | 5/2000 |
| WO | WO 01/55347 | 8/2001 |
| WO | WO 01/70988 | 9/2001 |
| WO | WO 01/80639 | 11/2001 |

OTHER PUBLICATIONS

Fajardo et al. Biological control: Theory and Applications in Pest Management; vol. 13 (3), pp. 143-151.*
Preston et al. MPMI (1995), vol. 8(5), pp. 717-732.*
Wei et al. Science (1992), vol. 257, and pp. 85-88.*
EL-Ghoauthi. Journal of Indust. Micro. Biotechnol (1997) 19: 160-162.*
Bhaskara Reddy et al. HortScience (1999), vol. 34, No. 3 p. 5440.*
Durner et al. Trends in Plant Science (1997), vol. 2(7):266-274.*
Pieterse et al. Trends in Plant Science (1999) 4:52-58.*
Dong et al. Plant J (1999) 20(2):207-215.*
Smilanick et al., "Virulence on Citrus of *Pseudomonas syringae* Strains That Control Postharvest Green Mold of Citrus. Fruit " *Plant Disease* 80(10):1123-1128 (1996).
Fajardo et al., "Biological Control: Theory and Applications in Pest Management," 13(3):143-51 (1998).
Abstract: Smilanick et al., "Virulence on Citrus of *Pseudomonas syringae* strains that control postharvest green mold of citrus fruit," Plant Disease 80(10):1123-1128 (1996).

* cited by examiner

*Primary Examiner* — Medina A Ibrahim
(74) *Attorney, Agent, or Firm* — LeClairRyan

(57) ABSTRACT

The present invention relates to a methods of inhibiting postharvest disease or desiccation in a fruit or vegetable, either by treating a fruit or vegetable with a hypersensitive response elicitor protein or polypeptide under conditions effective to inhibit postharvest disease or desiccation, or by providing a transgenic plant or plant seed transformed with a DNA molecule encoding a hypersensitive response elicitor polypeptide or protein and growing the transgenic plant or transgenic plant produced from the transgenic plant seed under conditions effective to inhibit a postharvest disease or desiccation in a fruit or vegetable harvested from the transgenic plant. Also disclosed are DNA constructs and expression systems, host cells, and transgenic plants containing the DNA construct.

21 Claims, No Drawings

TREATMENT OF FRUITS OR VEGETABLES WITH HYPERSENSITIVE RESPONSE ELICITOR TO INHIBIT POSTHARVEST DISEASE OR DESICCATION

This application is a continuation of Ser. No. 09/835,684, filed Apr. 16, 2001, now abandoned which claims benefit of U.S. Provisional Patent Application Ser. No. 60/198,359, filed Apr. 19, 2000. Each of these priority applications is hereby incorporated by reference in its entirety.

FIELD OF THE INVENTION

The present invention relates to methods of treating fruits or vegetables to inhibit postharvest diseases and/or desiccation of harvested fruits or vegetables.

BACKGROUND OF THE INVENTION

Postharvest diseases are often extensions of disease occurring in the field or orchard. Brown rot of stone fruits (*Monilinia Fructicola* (Wint.) Honey), for example, may cause blossom and twig blighting in the orchard. Infections in the orchard may not be visible at harvest if fruits are not refrigerated. *Colletotrichum gloeosporioiders* (Penz.) Arx may attack blossoms or leaves and young fruit of citrus, avocados, mangos, papayas, and a wide range of other tropical and subtropical species; infections in developing fruit are usually latent, and rot lesions appear only at the onset of fruit ripening. *Pezicula malicorticis* (Jacks.) Nannfld. causes cankers of limbs of apples and pears; infections in developing fruit are latent, and active rotting usually commences only after the fruit has spent several months in storage and proceeds during −1° C. storage because the organism is able to grow at very low temperatures. These fungi used as examples are able to penetrate the cuticle and epidermis of the fruit.

Whether capable of being penetrated directly or not, wounds are often the usual means by which the fungus enters fruit. Cuts, punctures, bruises, and abrasions cannot be avoided completely during harvest and handling. If the cuticle and epidermis are broken, spores find nutrients and humidity in fresh wounds ideal for spore germination and colonization. Separation of fruits from the parent plant at harvest creates an unavoidable wound that encourages stem-end rots.

Rots developing at the blossom end usually involve prior colonization of floral parts. For example, *Botrytis* blossom-end rot (*B. cinerea*) sometimes occurs in Bartlett pears after a month or two in storage at −1° C. Initiation of rot in fruit flesh is associated with old styles and stamens retained within the fruit. Floral infections occur in the senescing floral parts at the end of blossoming. Mostly these floral parts are invaded by *Alternaria* spp. and common saprophytic fungi, but *B. cinerea* also is found occasionally. Not all fruits having *B. cinerea*-invaded floral parts rot in storage, but a significant percentage do. By contrast, test fruits remain free from *Botrytis* blossom-end rot if the old floral parts of developing fruits are free from *B. cinerea*. Rotting of fruits in storage is greatly reduced by a single orchard spray with a fungicide at the end of blossoming.

Contact infection, by which mycelia grow from a rotting fruit to contact and penetrate nearby fruit, is an especially serious aspect of some very common postharvest pathogens. The ever-enlarging "nest" of rotting fruit tied together by fungus mycelia will involve all fruit in a container, if given sufficient time.

Disease or threat of disease dictates in large measure the manner in which perishable fruits are handled. In recent decades, fruits have been shipped to increasingly greater distances from points of production. Exploitation of these distant markets, however, may offer large economic benefits only if the life of the commodity is stretched to its limit. Diseases and disorders ordinarily manageable during handling and transcontinental transit and marketing may be excessive when transoceanic marine transport of longer duration is involved. Similarly, the extension of marketing periods by storing fruits until they near the end of their physiological life may cause additional disease problems. Losses are especially serious if they occur in market areas, because the costs of sorting, packaging, cooling, storage, and transportation, which may greatly exceed production costs, have already been incurred. Of even greater long-term importance may be an impaired reputation leading to reduced future sales.

Postharvest diseases of fruit cause 15 to 25% losses yearly in the fruit industry worldwide and much of this is due to rot caused by microorganisms. Fungicides, which have been the primary means of controlling postharvest diseases, have come under scrutiny as posing potential oncogenic risks when applied to processed foods. Thus, research efforts have been intensified to develop biological control procedures for postharvest diseases of fruits and vegetables that pose less risk to human health and the environment.

Considerable attention has been placed on assessing the use of antagonistic microorganisms as a viable alternative to the use of synthetic fungicides. Two basic approaches are available for using antagonistic microorganisms to control postharvest diseases. Naturally occurring antagonists that already exist on fruit and vegetable surfaces have been shown to control several rot pathogens on diverse commodities. Alternatively, artificially introduced antagonists have been shown to be effective in biologically controlling postharvest pathogens.

Since 1983, an explosion of research has occurred in the area of biological control of postharvest diseases by artificially introduced antagonists, mostly on fruit diseases (Janisiewicz, "Biological Control of Diseases of Fruit," *In Biocontrol of Plant Diseases II*, Mukergie et al. (ed.), CRC Press, Boca Raton, pp. 153-165 (1988) and Wilson et al., "Potential for Biological Control of Postharvest Plant Diseases," *Plant Disease* 69:375-378 (1985)). For example, rot on apples was controlled with yeast (Wisniewski et al., "Biological Control of Postharvest Diseases of Fruit: Inhibition of *Botrytis* Rot on Apples by an Antagonistic Yeast," *Proc. Electron Microsc. Soc. Am.* 46:290-91 (1988)), while brown rot in apricots was controlled with *Bacillus subtilis* (Pusey et al., "Postharvest Biological Control of Stone Fruit Brown Rot by *Bacillus subtilis*," *Plant Dis.* 68:753-56 (1984)). Mold incidence was reduced from 35% to 8% in lemon peel by a species of *Trichoderma* (De Matos, "Chemical and Microbiological Factors Influencing the Infection of Lemons by *Geotrichum candidum* and *Penicillium digitatum*," Ph.D. dissertation, University of California, Riverside, 106 pp. (1983)). Biocontrol of citrus rot pathogens was demonstrated with *Bacillus subtilis* (Singh et al., "*Bacillus subtilis* as a Control Agent Against Fungal Pathogens of Citrus Fruit," *Trans. Br. Mycol. Soc.* 83:487-90 (1984)). Such antagonists have various modes of action: antibiosis or competition for nutrients and space or both, induction of resistance in the host tissue, and direct interaction with the pathogen (Wilson et al., "Biological Control of Postharvest Diseases of Fruits and Vegetables: An Emerging Technology," *Annu. Rev. Phytopathol.* 27:425-441 (1989)).

While treatment with antagonistic bacterial or fungal species may be, at least to some extent, effective in controlling postharvest diseases, there are a number of factors which must be considered before this approach is used in commercial applications. First, the antagonists must be grown and maintained for use in treatments. This may result in significant expense and regulatory burdens depending on when and how frequently such antagonists would be applied. Also, it is questionable whether growers would want to maintain bioreactors for growing and propagating particular antagonist strains. Second, the efficacy of those antagonists may depend on storage conditions during shipment of harvested fruit. Some antagonists may not be able to tolerate variations in conditions during shipment, thereby allowing the pathogens to overcome any inhibitory effects of the antagonists. Given the above problems, it is not surprising that few of the antagonists reported to control plant pathogens have been successfully transferred from the laboratory into the field or postharvest environment.

Thus, there still exists a need to provide an effective, commercially viable method for treating fruits and vegetables to control postharvest diseases which avoids entirely or otherwise significantly reduces the need for fungicide treatments. In particular, it would be desirable to provide an effective, practicable treatment which presents little or no harm to humans or the environment.

The present invention is directed to overcoming these and other deficiencies in the art.

SUMMARY OF THE INVENTION

The present invention relates to a method of inhibiting postharvest disease or desiccation in a fruit or vegetable. This method is carried out treating a fruit or vegetable with a hypersensitive response elicitor protein or polypeptide under conditions effective to inhibit postharvest disease or desiccation.

A further aspect of the present invention relates to another method of inhibiting postharvest disease or desiccation in a fruit or vegetable. This method is carried out by providing a transgenic plant or plant seed transformed with a DNA molecule encoding a hypersensitive response elicitor polypeptide or protein and growing the transgenic plant or transgenic plant produced from the transgenic plant seed under conditions effective to inhibit a postharvest disease or desiccation in a fruit or vegetable harvested from the transgenic plant.

Another aspect of the present invention relates to a DNA construct that includes a DNA molecule encoding a hypersensitive response elicitor protein or polypeptide, a plant-expressible promoter operably coupled 5' to the DNA molecule, the promoter being effective to transcribe the DNA molecule in fruit or vegetable tissue, and a 3' regulatory region operably coupled to the DNA molecule, wherein expression of the DNA molecule in fruit or vegetable tissue imparts to a fruit or vegetable resistance against postharvest disease or desiccation. Also disclosed are expression systems, host cells, and transgenic plants which contain a heterologous DNA construct of the present invention.

By the present invention, the hypersensitive response elicitor protein or polypeptide can be used to inhibit or otherwise control postharvest diseases (i.e., caused by pathogens) in fruits or vegetables. Likewise, such treatment can also inhibit postharvest desiccation of treated fruits or vegetables. In achieving these objectives, the present invention enables produce growers, warehouse packers, shippers, and suppliers to process, handle, and store fruits and vegetables with reduced losses caused by postharvest disease and desiccation. As a result, the cost of bringing fruits and vegetables from the field to the consumer can be reduced. Importantly, the quality of the treated fruits or vegetables is improved.

DETAILED DESCRIPTION OF THE INVENTION

The present invention relates to a method of inhibiting postharvest disease or desiccation in a fruit or vegetable. This method is carried out treating a fruit or vegetable with a hypersensitive response elicitor protein or polypeptide under conditions effective to inhibit postharvest disease or desiccation.

A further aspect of the present invention relates to another method of inhibiting postharvest disease or desiccation in a fruit or vegetable. This method is carried out by providing a transgenic plant or plant seed transformed with a DNA molecule encoding a hypersensitive response elicitor polypeptide or protein and growing the transgenic plant or transgenic plant produced from the transgenic plant seed under conditions effective to inhibit a postharvest disease or desiccation in a fruit or vegetable harvested from the transgenic plant.

For use in accordance with these methods, suitable hypersensitive response elicitor proteins or polypeptides are those derived from a wide variety of bacterial and fungal pathogens, preferably bacterial pathogens.

Exemplary hypersensitive response elicitor proteins and polypeptides from bacterial sources include, without limitation, the hypersensitive response elicitors derived from *Erwinia* species (e.g., *Erwinia amylovora*, *Erwinia chrysanthemi*, *Erwinia stewartii*, *Erwinia carotovora*, etc.), *Pseudomonas* species (e.g., *Pseudomonas syringae*, *Pseudomonas solanacearum*, etc.), and *Xanthomonas* species (e.g., *Xanthomonas campestris*). In addition to hypersensitive response elicitors from these Gram-negative bacteria, it is possible to use elicitors derived from Gram-positive bacteria. One example is the hypersensitive response elicitor derived from *Clavibacter michiganensis* subsp. *sepedonicus*.

Exemplary hypersensitive response elicitor proteins or polypeptides from fungal sources include, without limitation, the hypersensitive response elicitors (i.e., elicitins) from various *Phytophthora* species (e.g., *Phytophthora parasitica*, *Phytophthora cryptogea*, *Phytophthora cinnamomi*, *Phytophthora capsici*, *Phytophthora megasperma*, *Phytophthora citrophthora*, etc.).

Preferably, the hypersensitive response elicitor protein or polypeptide is derived from *Erwinia chrysanthemi*, *Erwinia amylovora*, *Pseudomonas syringae*, or *Pseudomonas solanacearum*.

A hypersensitive response elicitor protein or polypeptide from *Erwinia chrysanthemi* has an amino acid sequence corresponding to SEQ. ID. No. 1 as follows:

```
Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
                20                  25                  30

Leu Gly Ser Ser Val Asp Lys Leu Ser Ser Thr Ile Asp Lys Leu Thr
                35                  40                  45
```

```
Ser Ala Leu Thr Ser Met Met Phe Gly Gly Ala Leu Ala Gln Gly Leu
     50                  55                  60
Gly Ala Ser Ser Lys Gly Leu Gly Met Ser Asn Gln Leu Gly Gln Ser
 65                  70                  75                  80
Phe Gly Asn Gly Ala Gln Gly Ala Ser Asn Leu Leu Ser Val Pro Lys
                 85                  90                  95
Ser Gly Gly Asp Ala Leu Ser Lys Met Phe Asp Lys Ala Leu Asp Asp
                100                 105                 110
Leu Leu Gly His Asp Thr Val Thr Lys Leu Thr Asn Gln Ser Asn Gln
            115                 120                 125
Leu Ala Asn Ser Met Leu Asn Ala Ser Gln Met Thr Gln Gly Asn Met
        130                 135                 140
Asn Ala Phe Gly Ser Gly Val Asn Asn Ala Leu Ser Ser Ile Leu Gly
145                 150                 155                 160
Asn Gly Leu Gly Gln Ser Met Ser Gly Phe Ser Gln Pro Ser Leu Gly
                165                 170                 175
Ala Gly Gly Leu Gln Gly Leu Ser Gly Ala Gly Ala Phe Asn Gln Leu
                180                 185                 190
Gly Asn Ala Ile Gly Met Gly Val Gly Gln Asn Ala Ala Leu Ser Ala
            195                 200                 205
Leu Ser Asn Val Ser Thr His Val Asp Gly Asn Asn Arg His Phe Val
        210                 215                 220
Asp Lys Glu Asp Arg Gly Met Ala Lys Glu Ile Gly Gln Phe Met Asp
225                 230                 235                 240
Gln Tyr Pro Glu Ile Phe Gly Lys Pro Glu Tyr Gln Lys Asp Gly Trp
                245                 250                 255
Ser Ser Pro Lys Thr Asp Asp Lys Ser Trp Ala Lys Ala Leu Ser Lys
                260                 265                 270
Pro Asp Asp Asp Gly Met Thr Gly Ala Ser Met Asp Lys Phe Arg Gln
            275                 280                 285
Ala Met Gly Met Ile Lys Ser Ala Val Ala Gly Asp Thr Gly Asn Thr
        290                 295                 300
Asn Leu Asn Leu Arg Gly Ala Gly Gly Ala Ser Leu Gly Ile Asp Ala
305                 310                 315                 320
Ala Val Val Gly Asp Lys Ile Ala Asn Met Ser Leu Gly Lys Leu Ala
                325                 330                 335
Asn Ala
```

This hypersensitive response elicitor protein or polypeptide has a molecular weight of 34 kDa, is heat stable, has a glycine content of greater than 16%, and contains substantially no cysteine. This *Erwinia chrysanthemi* hypersensitive response elicitor protein or polypeptide is encoded by a DNA molecule having a nucleotide sequence corresponding to SEQ. ID. No. 2 as follows:

```
cgatttacc cgggtgaacg tgctatgacc gacagcatca cggtattcga caccgttacg   60
gcgtttatgg ccgcgatgaa ccggcatcag gcggcgcgct ggtcgccgca atccggcgtc  120
gatctggtat ttcagtttgg ggacaccggg cgtgaactca tgatgcagat tcagccgggg  180
cagcaatatc ccggcatgtt gcgcacgctg ctcgctcgtc gttatcagca ggcggcagag  240
tgcgatggct gccatctgtg cctgaacggc agcgatgtat tgatcctctg gtggccgctg  300
ccgtcggatc ccggcagtta tccgcaggtg atcgaacgtt tgtttgaact ggcgggaatg  360
```

```
acgttgccgt cgctatccat agcaccgacg gcgcgtccgc agacagggaa cggacgcgcc    420
cgatcattaa gataaaggcg gcttttttta ttgcaaaacg gtaacggtga ggaaccgttt    480
caccgtcggc gtcactcagt aacaagtatc catcatgatg cctacatcgg gatcggcgtg    540
ggcatccgtt gcagatactt ttgcgaacac ctgacatgaa tgaggaaacg aaattatgca    600
aattacgatc aaagcgcaca tcggcggtga tttgggcgtc tccggtctgg ggctgggtgc    660
tcagggactg aaaggactga attccgcggc ttcatcgctg ggttccagcg tggataaact    720
gagcagcacc atcgataagt tgacctccgc gctgacttcg atgatgtttg gcggcgcgct    780
ggcgcagggg ctgggcgcca gctcgaaggg gctggggatg agcaatcaac tgggccagtc    840
tttcggcaat ggcgcgcagg gtgcgagcaa cctgctatcc gtaccgaaat ccggcggcga    900
tgcgttgtca aaaatgtttg ataaagcgct ggacgatctg ctgggtcatg acaccgtgac    960
caagctgact aaccagagca accaactggc taattcaatg ctgaacgcca gccagatgac   1020
ccagggtaat atgaatgcgt tcggcagcgg tgtgaacaac gcactgtcgt ccattctcgg   1080
caacggtctc ggccagtcga tgagtggctt ctctcagcct tctctggggg caggcggctt   1140
gcagggcctg agcggcgcgg gtgcattcaa ccagttgggt aatgccatcg gcatgggcgt   1200
ggggcagaat gctgcgctga gtgcgttgag taacgtcagc acccacgtag acggtaacaa   1260
ccgccacttt gtagataaag aagatcgcgg catggcgaaa gagatcggcc agtttatgga   1320
tcagtatccg gaaatattcg gtaaaccgga ataccagaaa gatggctgga gttcgccgaa   1380
gacggacgac aaatcctggg ctaaagcgct gagtaaaccg gatgatgacg gtatgaccgg   1440
cgccagcatg gacaaattcc gtcaggcgat gggtatgatc aaaagcgcgg tggcgggtga   1500
taccggcaat accaacctga acctgcgtgg cgcgggcggt gcatcgctgg gtatcgatgc   1560
ggctgtcgtc ggcgataaaa tagccaacat gtcgctgggg aagctggcca acgcctgata   1620
atctgtgctg gcctgataaa gcggaaacga aaaagagac ggggaagcct gtctcttttc    1680
ttattatgcg gtttatgcgg ttacctggac cggttaatca tcgtcatcga tctggtacaa   1740
acgcacattt tcccgttcat tcgcgtcgtt acgcgccaca atcgcgatgg catcttcctc   1800
gtcgctcaga ttgcgcggct gatggggaac gccgggtgga atatagagaa actcgccggc   1860
cagatggaga cacgtctgcg ataaatctgt gccgtaacgt gtttctatcc gcccctttag   1920
cagatagatt gcggtttcgt aatcaacatg gtaatgcggt tccgcctgtg cgccggccgg   1980
gatcaccaca atattcatag aaagctgtct tgcacctacc gtatcgcggg agataccgac   2040
aaaatagggc agttttttgcg tggtatccgt ggggtgttcc ggcctgacaa tcttgagttg   2100
gttcgtcatc atctttctcc atctgggcga cctgatcggt t                        2141
```

The above nucleotide and amino acid sequences are disclosed and further described in U.S. Pat. No. 5,850,015 to Bauer et al. and U.S. Pat. No. 5,776,889 to Wei et al., which are hereby incorporated by reference in their entirety.

A hypersensitive response elicitor protein or polypeptide derived from *Erwinia amylovora* has an amino acid sequence corresponding to SEQ. ID. No. 3 as follows:

```
Met Ser Leu Asn Thr Ser Gly Leu Gly Ala Ser Thr Met Gln Ile Ser
1               5                   10                  15

Ile Gly Gly Ala Gly Gly Asn Asn Gly Leu Leu Gly Thr Ser Arg Gln
            20                  25                  30

Asn Ala Gly Leu Gly Gly Asn Ser Ala Leu Gly Leu Gly Gly Gly Asn
        35                  40                  45
```

-continued

```
Gln Asn Asp Thr Val Asn Gln Leu Ala Gly Leu Leu Thr Gly Met Met
 50                  55                  60

Met Met Met Ser Met Met Gly Gly Gly Gly Leu Met Gly Gly Gly Leu
 65                  70                  75                  80

Gly Gly Gly Leu Gly Asn Gly Leu Gly Gly Ser Gly Gly Leu Gly Glu
                 85                  90                  95

Gly Leu Ser Asn Ala Leu Asn Asp Met Leu Gly Gly Ser Leu Asn Thr
                100                 105                 110

Leu Gly Ser Lys Gly Gly Asn Thr Thr Ser Thr Thr Asn Ser Pro
            115                 120                 125

Leu Asp Gln Ala Leu Gly Ile Asn Ser Thr Ser Gln Asn Asp Asp Ser
            130                 135                 140

Thr Ser Gly Thr Asp Ser Thr Ser Asp Ser Ser Asp Pro Met Gln Gln
145                 150                 155                 160

Leu Leu Lys Met Phe Ser Glu Ile Met Gln Ser Leu Phe Gly Asp Gly
                165                 170                 175

Gln Asp Gly Thr Gln Gly Ser Ser Ser Gly Gly Lys Gln Pro Thr Glu
                180                 185                 190

Gly Glu Gln Asn Ala Tyr Lys Lys Gly Val Thr Asp Ala Leu Ser Gly
            195                 200                 205

Leu Met Gly Asn Gly Leu Ser Gln Leu Leu Gly Asn Gly Gly Leu Gly
            210                 215                 220

Gly Gly Gln Gly Gly Asn Ala Gly Thr Gly Leu Asp Gly Ser Ser Leu
225                 230                 235                 240

Gly Gly Lys Gly Leu Gln Asn Leu Ser Gly Pro Val Asp Tyr Gln Gln
                245                 250                 255

Leu Gly Asn Ala Val Gly Thr Gly Ile Gly Met Lys Ala Gly Ile Gln
            260                 265                 270

Ala Leu Asn Asp Ile Gly Thr His Arg His Ser Ser Thr Arg Ser Phe
            275                 280                 285

Val Asn Lys Gly Asp Arg Ala Met Ala Lys Glu Ile Gly Gln Phe Met
            290                 295                 300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330                 335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
            355                 360                 365

Gly Asn Leu Gln Ala Arg Gly Ala Gly Gly Ser Ser Leu Gly Ile Asp
            370                 375                 380

Ala Met Met Ala Gly Asp Ala Ile Asn Asn Met Ala Leu Gly Lys Leu
385                 390                 395                 400

Gly Ala Ala
```

This hypersensitive response elicitor protein or polypeptide has a molecular weight of about 39 kDa, has a pI of approximately 4.3, and is heat stable at 100° C. for at least 10 minutes. This hypersensitive response elicitor protein or polypeptide has substantially no cysteine. The hypersensitive response elicitor protein or polypeptide derived from *Erwinia amylovora* is more fully described in Wei, Z-M., et al., "Harpin, Elicitor of the Hypersensitive Response Produced by the Plant Pathogen *Erwinia amylovora*," *Science* 257:85-88 (1992), which is hereby incorporated by reference in its entirety. The DNA molecule encoding this hypersensitive response elicitor protein or polypeptide has a nucleotide sequence corresponding to SEQ. ID. No. 4 as follows:

```
aagcttcggc atggcacgtt tgaccgttgg gtcggcaggg tacgtttgaa ttattcataa     60
gaggaatacg ttatgagtct gaatacaagt gggctgggag cgtcaacgat gcaaatttct    120
atcggcggtg cgggcggaaa taacgggttg ctgggtacca gtcgccagaa tgctgggttg    180
ggtggcaatt ctgcactggg gctgggcggc ggtaatcaaa atgataccgt caatcagctg    240
gctggcttac tcaccggcat gatgatgatg atgagcatga tgggcggtgg tgggctgatg    300
ggcggtggct taggcggtgg cttaggtaat ggcttgggtg gctcaggtgg cctgggcgaa    360
ggactgtcga acgcgctgaa cgatatgtta ggcggttcgc tgaacacgct gggctcgaaa    420
ggcggcaaca ataccacttc aacaacaaat tccccgctgg accaggcgct gggtattaac    480
tcaacgtccc aaaacgacga ttccacctcc ggcacagatt ccacctcaga ctccagcgac    540
ccgatgcagc agctgctgaa gatgttcagc gagataatgc aaagcctgtt tggtgatggg    600
caagatggca cccagggcag ttcctctggg ggcaagcagc cgaccgaagg cgagcagaac    660
gcctataaaa aaggagtcac tgatgcgctg tcgggcctga tgggtaatgg tctgagccag    720
ctccttggca acgggggact gggaggtggt cagggcggta atgctggcac gggtcttgac    780
ggttcgtcgc tgggcggcaa agggctgcaa aacctgagcg ggccggtgga ctaccagcag    840
ttaggtaacg ccgtgggtac cggtatcggt atgaaagcgg gcattcaggc gctgaatgat    900
atcggtacgc acaggcacag ttcaaccogt tctttcgtca ataaaggcga tcgggcgatg    960
gcgaaggaaa tcggtcagtt catggaccag tatcctgagg tgtttggcaa gccgcagtac   1020
cagaaaggcc cgggtcagga ggtgaaaacc gatgacaaat catgggcaaa agcactgagc   1080
aagccagatg acgacggaat gacaccagcc agtatggagc agttcaacaa agccaagggc   1140
atgatcaaaa ggcccatggc gggtgatacc ggcaacggca acctgcaggc acgcggtgcc   1200
ggtggttctt cgctgggtat tgatgccatg atggccggtg atgccattaa caatatggca   1260
cttggcaagc tgggcgcggc ttaagctt                                       1288
```

The above nucleotide and amino acid sequences are disclosed are further described in U.S. Pat. No. 5,849,868 to Beer et al. and U.S. Pat. No. 5,776,889 to Wei et al., which are hereby incorporated by reference in their entirety.

Another hypersensitive response elicitor protein or polypeptide derived from *Erwinia amylovora* has an amino acid sequence corresponding to SEQ. ID. No. 5 as follows:

```
Met Ser Ile Leu Thr Leu Asn Asn Asn Thr Ser Ser Ser Pro Gly Leu
1               5                   10                  15

Phe Gln Ser Gly Gly Asp Asn Gly Leu Gly Gly His Asn Ala Asn Ser
                20                  25                  30

Ala Leu Gly Gln Gln Pro Ile Asp Arg Gln Thr Ile Glu Gln Met Ala
            35                  40                  45

Gln Leu Leu Ala Glu Leu Leu Lys Ser Leu Leu Ser Pro Gln Ser Gly
        50                  55                  60

Asn Ala Ala Thr Gly Ala Gly Gly Asn Asp Gln Thr Thr Gly Val Gly
65              70                  75                  80
```

-continued

Asn Ala Gly Gly Leu Asn Gly Arg Lys Gly Thr Ala Gly Thr Thr Pro
            85                  90                  95

Gln Ser Asp Ser Gln Asn Met Leu Ser Glu Met Gly Asn Asn Gly Leu
           100                 105                 110

Asp Gln Ala Ile Thr Pro Asp Gly Gln Gly Gly Gln Ile Gly Asp
       115                 120                 125

Asn Pro Leu Leu Lys Ala Met Leu Lys Leu Ile Ala Arg Met Met Asp
130                 135                 140

Gly Gln Ser Asp Gln Phe Gly Gln Pro Gly Thr Gly Asn Asn Ser Ala
145                 150                 155                 160

Ser Ser Gly Thr Ser Ser Gly Gly Ser Pro Phe Asn Asp Leu Ser
           165                 170                 175

Gly Gly Lys Ala Pro Ser Gly Asn Ser Pro Ser Gly Asn Tyr Ser Pro
           180                 185                 190

Val Ser Thr Phe Ser Pro Pro Ser Thr Pro Thr Ser Pro Thr Ser Pro
           195                 200                 205

Leu Asp Phe Pro Ser Ser Pro Thr Lys Ala Ala Gly Gly Ser Thr Pro
       210                 215                 220

Val Thr Asp His Pro Asp Pro Val Gly Ser Ala Gly Ile Gly Ala Gly
225                 230                 235                 240

Asn Ser Val Ala Phe Thr Ser Ala Gly Ala Asn Gln Thr Val Leu His
           245                 250                 255

Asp Thr Ile Thr Val Lys Ala Gly Gln Val Phe Asp Gly Lys Gly Gln
           260                 265                 270

Thr Phe Thr Ala Gly Ser Glu Leu Gly Asp Gly Gln Ser Glu Asn
           275                 280                 285

Gln Lys Pro Leu Phe Ile Leu Glu Asp Gly Ala Ser Leu Lys Asn Val
           290                 295                 300

Thr Met Gly Asp Asp Gly Ala Asp Gly Ile His Leu Tyr Gly Asp Ala
305                 310                 315                 320

Lys Ile Asp Asn Leu His Val Thr Asn Val Gly Glu Asp Ala Ile Thr
               325                 330                 335

Val Lys Pro Asn Ser Ala Gly Lys Lys Ser His Val Glu Ile Thr Asn
           340                 345                 350

Ser Ser Phe Glu His Ala Ser Asp Lys Ile Leu Gln Leu Asn Ala Asp
           355                 360                 365

Thr Asn Leu Ser Val Asp Asn Val Lys Ala Lys Asp Phe Gly Thr Phe
       370                 375                 380

Val Arg Thr Asn Gly Gly Gln Gln Gly Asn Trp Asp Leu Asn Leu Ser
385                 390                 395                 400

His Ile Ser Ala Glu Asp Gly Lys Phe Ser Phe Val Lys Ser Asp Ser
           405                 410                 415

Glu Gly Leu Asn Val Asn Thr Ser Asp Ile Ser Leu Gly Asp Val Glu
           420                 425                 430

Asn His Tyr Lys Val Pro Met Ser Ala Asn Leu Lys Val Ala Glu
           435                 440                 445

This protein or polypeptide is acidic, rich in glycine and serine, and lacks cysteine. It is also heat stable, protease sensitive, and suppressed by inhibitors of plant metabolism. The protein or polypeptide of the present invention has a predicted molecular size of ca. 4.5 kDa. The DNA molecule encoding this hypersensitive response elicitor protein or polypeptide has a nucleotide sequence corresponding to SEQ. ID. No. 6 as follows:

```
atgtcaattc ttacgcttaa caacaatacc tcgtcctcgc cgggtctgtt ccagtccggg    60
ggggacaacg ggcttggtgg tcataatgca aattctgcgt tggggcaaca acccatcgat   120
cggcaaacca ttgagcaaat ggctcaatta ttggcggaac tgttaaagtc actgctatcg   180
ccacaatcag gtaatgcggc aaccggagcc ggtggcaatg accagactac aggagttggt   240
aacgctggcg gcctgaacgg acgaaaaggc acagcaggaa ccactccgca gtctgacagt   300
cagaacatgc tgagtgagat gggcaacaac gggctggatc aggccatcac gcccgatggc   360
cagggcggcg ggcagatcgg cgataatcct ttactgaaag ccatgctgaa gcttattgca   420
cgcatgatgg acggccaaag cgatcagttt ggccaacctg gtacgggcaa caacagtgcc   480
tcttccggta cttcttcatc tggcggttcc ccttttaacg atctatcagg ggggaaggcc   540
ccttccggca actcccctt c cggcaactac tctcccgtca gtaccttctc acccccatcc   600
acgccaacgt cccctacctc accgcttgat ttcccttctt ctcccaccaa agcagccggg   660
ggcagcacgc cggtaaccga tcatcctgac cctgttggta gcgcgggcat cggggccgga   720
aattcggtgg ccttcaccag cgccggcgct aatcagacgg tgctgcatga caccattacc   780
gtgaaagcgg gtcaggtgtt tgatggcaaa ggacaaacct tcaccgccgg ttcagaatta   840
ggcgatggcg gccagtctga aaaccagaaa ccgctgttta tactggaaga cggtgccagc   900
ctgaaaaacg tcaccatggg cgacgacggg gcggatggta ttcatcttta cggtgatgcc   960
aaaatagaca atctgcacgt caccaacgtg ggtgaggacg cgattaccgt taagccaaac  1020
agcgcgggca aaaaatccca cgttgaaatc actaacagtt ccttcgagca cgcctctgac  1080
aagatcctgc agctgaatgc cgatactaac ctgagcgttg acaacgtgaa ggccaaagac  1140
tttggtactt ttgtacgcac taacggcggt caacagggta actgggatct gaatctgagc  1200
catatcagcg cagaagacgg taagttctcg ttcgttaaaa gcgatagcga ggggctaaac  1260
gtcaatacca gtgatatctc actgggtgat gttgaaaacc actacaaagt gccgatgtcc  1320
gccaacctga aggtggctga atga                                         1344
```

The above nucleotide and amino acid sequences are disclosed and further described in U.S. patent application Ser. No. 09/120,927 to Beer et al., which is hereby incorporated by reference in its entirety.

A hypersensitive response elicitor protein or polypeptide derived from *Pseudomonas syringae* has an amino acid sequence corresponding to SEQ. ID. No. 7 as follows:

```
Met Gln Ser Leu Ser Leu Asn Ser Ser Ser Leu Gln Thr Pro Ala Met
1               5                   10                  15

Ala Leu Val Leu Val Arg Pro Glu Ala Glu Thr Thr Gly Ser Thr Ser
            20                  25                  30

Ser Lys Ala Leu Gln Glu Val Val Val Lys Leu Ala Glu Glu Leu Met
        35                  40                  45

Arg Asn Gly Gln Leu Asp Asp Ser Ser Pro Leu Gly Lys Leu Leu Ala
    50                  55                  60

Lys Ser Met Ala Ala Asp Gly Lys Ala Gly Gly Gly Ile Glu Asp Val
65                  70                  75                  80

Ile Ala Ala Leu Asp Lys Leu Ile His Glu Lys Leu Gly Asp Asn Phe
                85                  90                  95
```

```
Gly Ala Ser Ala Asp Ser Ala Ser Gly Thr Gly Gln Gln Asp Leu Met
            100                 105                 110
Thr Gln Val Leu Asn Gly Leu Ala Lys Ser Met Leu Asp Asp Leu Leu
        115                 120                 125
Thr Lys Gln Asp Gly Gly Thr Ser Phe Ser Glu Asp Asp Met Pro Met
    130                 135                 140
Leu Asn Lys Ile Ala Gln Phe Met Asp Asp Asn Pro Ala Gln Phe Pro
145                 150                 155                 160
Lys Pro Asp Ser Gly Ser Trp Val Asn Glu Leu Lys Glu Asp Asn Phe
                165                 170                 175
Leu Asp Gly Asp Glu Thr Ala Ala Phe Arg Ser Ala Leu Asp Ile Ile
                180                 185                 190
Gly Gln Gln Leu Gly Asn Gln Gln Ser Asp Ala Gly Ser Leu Ala Gly
            195                 200                 205
Thr Gly Gly Gly Leu Gly Thr Pro Ser Ser Phe Ser Asn Asn Ser Ser
    210                 215                 220
Val Met Gly Asp Pro Leu Ile Asp Ala Asn Thr Gly Pro Gly Asp Ser
225                 230                 235                 240
Gly Asn Thr Arg Gly Glu Ala Gly Gln Leu Ile Gly Glu Leu Ile Asp
                245                 250                 255
Arg Gly Leu Gln Ser Val Leu Ala Gly Gly Leu Gly Thr Pro Val
                260                 265                 270
Asn Thr Pro Gln Thr Gly Thr Ser Ala Asn Gly Gly Gln Ser Ala Gln
        275                 280                 285
Asp Leu Asp Gln Leu Leu Gly Gly Leu Leu Leu Lys Gly Leu Glu Ala
        290                 295                 300
Thr Leu Lys Asp Ala Gly Gln Thr Gly Thr Asp Val Gln Ser Ser Ala
305                 310                 315                 320
Ala Gln Ile Ala Thr Leu Leu Val Ser Thr Leu Leu Gln Gly Thr Arg
                325                 330                 335
Asn Gln Ala Ala Ala
            340
```

This hypersensitive response elicitor protein or polypeptide has a molecular weight of 34-35 kDa. It is rich in glycine (about 13.5%) and lacks cysteine and tyrosine. Further information about the hypersensitive response elicitor derived from *Pseudomonas syringae* is found in He, S. Y., et al., "*Pseudomonas syringae* pv. *syringae* Harpin$_{Pss}$: a Protein that is Secreted via the Hrp Pathway and Elicits the Hypersensitive Response in Plants," *Cell* 73:1255-1266 (1993), which is hereby incorporated by reference in its entirety. The DNA molecule encoding this hypersensitive response elicitor from *Pseudomonas syringae* has a nucleotide sequence corresponding to SEQ. ID. No. 8 as follows:

```
atgcagagtc tcagtcttaa cagcagctcg ctgcaaaccc cggcaatggc ccttgtcctg    60
gtacgtcctg aagccgagac gactggcagt acgtcgagca aggcgcttca ggaagttgtc   120
gtgaagctgg ccgaggaact gatgcgcaat ggtcaactcg acgacagctc gccattggga   180
aaactgttgg ccaagtcgat ggccgcagat ggcaaggcgg gcggcggtat tgaggatgtc   240
atcgctgcgc tggacaagct gatccatgaa aagctcggtg acaacttcgg cgcgtctgcg   300
gacagcgcct cgggtaccgg acagcaggac ctgatgactc aggtgctcaa tggcctggcc   360
aagtcgatgc tcgatgatct tctgaccaag caggatggcg ggacaagctt ctccgaagac   420
gatatgccga tgctgaacaa gatcgcgcag ttcatggatg acaatcccgc acagtttccc   480
aagccggact cgggctcctg ggtgaacgaa ctcaaggaag acaacttcct tgatggcgac   540
gaaacggctg cgttccgttc ggcactcgac atcattggcc agcaactggg taatcagcag   600
agtgacgctg gcagtctggc agggacgggt ggaggtctgg gcactccgag cagttttttcc   660
```

-continued

```
aacaactcgt ccgtgatggg tgatccgctg atcgacgcca ataccggtcc cggtgacagc    720
ggcaataccc gtggtgaagc ggggcaactg atcggcgagc ttatcgaccg tggcctgcaa    780
tcggtattgg ccggtggtgg actgggcaca cccgtaaaca ccccgcagac cggtacgtcg    840
gcgaatggcg gacagtccgc tcaggatctt gatcagttgc tgggcggctt gctgctcaag    900
ggcctggagg caacgctcaa ggatgccggg caaacaggca ccgacgtgca gtcgagcgct    960
gcgcaaatcg ccaccttgct ggtcagtacg ctgctgcaag gcacccgcaa tcaggctgca   1020
gcctga                                                              1026
```

The above nucleotide and amino acid sequences are disclosed and further described in U.S. Pat. No. 5,708,139 to Collmer et al. and U.S. Pat. No. 5,776,889 to Wei et al., which are hereby incorporated by reference in their entirety.

Another hypersensitive response elicitor protein or polypeptide derived from *Pseudomonas syringae* has an amino acid sequence corresponding to SEQ. ID. No. 9 as follows:

```
Met Ser Ile Gly Ile Thr Pro Arg Pro Gln Gln Thr Thr Thr Pro Leu
1               5                   10                  15

Asp Phe Ser Ala Leu Ser Gly Lys Ser Pro Gln Pro Asn Thr Phe Gly
                20                  25                  30

Glu Gln Asn Thr Gln Gln Ala Ile Asp Pro Ser Ala Leu Leu Phe Gly
                35                  40                  45

Ser Asp Thr Gln Lys Asp Val Asn Phe Gly Thr Pro Asp Ser Thr Val
            50                  55                  60

Gln Asn Pro Gln Asp Ala Ser Lys Pro Asn Asp Ser Gln Ser Asn Ile
65                  70                  75                  80

Ala Lys Leu Ile Ser Ala Leu Ile Met Ser Leu Leu Gln Met Leu Thr
                85                  90                  95

Asn Ser Asn Lys Lys Gln Asp Thr Asn Gln Glu Gln Pro Asp Ser Gln
                100                 105                 110

Ala Pro Phe Gln Asn Asn Gly Gly Leu Gly Thr Pro Ser Ala Asp Ser
                115                 120                 125

Gly Gly Gly Gly Thr Pro Asp Ala Thr Gly Gly Gly Gly Asp Thr
            130                 135                 140

Pro Ser Ala Thr Gly Gly Gly Gly Asp Thr Pro Thr Ala Thr Gly
145                 150                 155                 160

Gly Gly Gly Ser Gly Gly Gly Thr Pro Thr Ala Thr Gly Gly
                165                 170                 175

Ser Gly Gly Thr Pro Thr Ala Thr Gly Gly Glu Gly Val Thr
            180                 185                 190

Pro Gln Ile Thr Pro Gln Leu Ala Asn Pro Asn Arg Thr Ser Gly Thr
            195                 200                 205

Gly Ser Val Ser Asp Thr Ala Gly Ser Thr Glu Gln Ala Gly Lys Ile
            210                 215                 220

Asn Val Val Lys Asp Thr Ile Lys Val Gly Ala Gly Glu Val Phe Asp
225                 230                 235                 240

Gly His Gly Ala Thr Phe Thr Ala Asp Lys Ser Met Gly Asn Gly Asp
                245                 250                 255

Gln Gly Glu Asn Gln Lys Pro Met Phe Glu Leu Ala Glu Gly Ala Thr
                260                 265                 270

Leu Lys Asn Val Asn Leu Gly Glu Asn Glu Val Asp Gly Ile His Val
            275                 280                 285

Lys Ala Lys Asn Ala Gln Glu Val Thr Ile Asp Asn Val His Ala Gln
            290                 295                 300

Asn Val Gly Glu Asp Leu Ile Thr Val Lys Gly Glu Gly Gly Ala Ala
305                 310                 315                 320
```

```
Val Thr Asn Leu Asn Ile Lys Asn Ser Ser Ala Lys Gly Ala Asp Asp
            325                 330                 335

Lys Val Val Gln Leu Asn Ala Asn Thr His Leu Lys Ile Asp Asn Phe
            340                 345                 350

Lys Ala Asp Asp Phe Gly Thr Met Val Arg Thr Asn Gly Gly Lys Gln
            355                 360                 365

Phe Asp Asp Met Ser Ile Glu Leu Asn Gly Ile Glu Ala Asn His Gly
            370                 375                 380

Lys Phe Ala Leu Val Lys Ser Asp Ser Asp Asp Leu Lys Leu Ala Thr
385                 390                 395                 400

Gly Asn Ile Ala Met Thr Asp Val Lys His Ala Tyr Asp Lys Thr Gln
            405                 410                 415

Ala Ser Thr Gln His Thr Glu Leu
            420
```

This protein or polypeptide is acidic, glycine-rich, lacks cysteine, and is deficient in aromatic amino acids. The DNA molecule encoding this hypersensitive response elicitor from *Pseudomonas syringae* has a nucleotide sequence corresponding to SEQ. ID. No. 10 as follows:

```
tccacttcg

-continued

```
tcgcaccaac ggtggcaagc agtttgatga catgagcatc gagctgaacg gcatcgaagc    1560
taaccacggc aagttcgccc tggtgaaaag cgacagtgac gatctgaagc tggcaacggg    1620
caacatcgcc atgaccgacg tcaaacacgc ctacgataaa acccaggcat cgacccaaca    1680
caccgagctt tgaatccaga caagtagctt gaaaaaaggg ggtggactc                1729
```

The above nucleotide and amino acid sequences are disclosed and further described in U.S. patent application Ser. No. 09/120,817 to Collmer et al., which is hereby incorporated by reference in its entirety.

A hypersensitive response elicitor protein or polypeptide derived from *Pseudomonas solanacearum* has an amino acid sequence corresponding to SEQ. ID. No. 11 as follows:

```
Met

```
                     -continued
Val Gln Ile Leu Gln Gln Met Leu Ala Ala Gln Asn Gly Gly Ser Gln
            325                 330                 335

Gln Ser Thr Ser Thr Gln Pro Met
        340
```

Further information regarding this hypersensitive response elicitor protein or polypeptide derived from *Pseudomonas solanacearum* is set forth in Arlat, M., et al., "PopA1, a Protein which Induces a Hypersensitive-like Response in Specific Petunia Genotypes, is Secreted via the Hrp Pathway of *Pseudomonas solanacearum*," *EMBO J.* 13:543-533 (1994), which is hereby incorporated by reference in its entirety. It is encoded by a DNA molecule from *Pseudomonas solanacearum* having a nucleotide sequence corresponding SEQ. ID. No. 12 as follows:

nicity of *Erwinia stewartii* on Maize," *Ann. Mtg. Am. Phytopath. Soc.*, Jul. 27-31, 1996, which are hereby incorporated by reference in their entirety.

Hypersensitive response elicitor proteins or polypeptides from various *Phytophthora* species are described in Kaman, et al., "Extracellular Protein Elicitors from *Phytophthora*: Most Specificity and Induction of Resistance to Bacterial and Fungal Phytopathogens," *Molec. Plant-Microbe Interact.*, 6(1):15-25 (1993); Ricci, et al., "Structure and Activity of Proteins from Pathogenic Fungi *Phytophthora* Eliciting

```
atgtcagtcg gaaacatcca gagcccgtcg aacctcccgg gtctgcagaa cctgaacctc      60
aacaccaaca ccaacagcca gcaatcgggc cagtccgtgc aagacctgat caagcaggtc     120
gagaaggaca tcctcaacat catcgcagcc ctcgtgcaga aggccgcaca gtcggcgggc     180
ggcaacaccg gtaacaccgg caacgcgccg gcgaaggacg gcaatgccaa cgcgggcgcc     240
aacgacccga gcaagaacga cccgagcaag agccaggctc cgcagtcggc caacaagacc     300
ggcaacgtcg acgacgccaa caaccaggat ccgatgcaag cgctgatgca gctgctggaa     360
gacctggtga agctgctgaa ggcggccctg cacatgcagc agcccggcgg caatgacaag     420
ggcaacggcg tgggcggtgc caacgcgcc  aagggtgccg gcggccaggg cggcctggcc     480
gaagcgctgc aggagatcga gcagatcctc gcccagctcg gcggcggcgg tgctggcgcc     540
ggcggcgcgg gtggcggtgt cggcggtgct ggtggcgcgg atggcggctc cggtgcgggt     600
ggcgcaggcg gtgcgaacgg cgccgacggc ggcaatggcg tgaacggcaa ccaggcgaac     660
ggcccgcaga acgcaggcga tgtcaacggt gccaacggcg cggatgacgg cagcgaagac     720
cagggcggcc tcaccggcgt gctgcaaaag ctgatgaaga tcctgaacgc gctggtgcag     780
atgatgcagc aaggcggcct cggcggcggc aaccaggcgc agggcggctc gaagggtgcc     840
ggcaacgcct cgccggcttc cggcgcgaac ccgggcgcga accagccgg  ttcggcggat     900 gatcaatcgt ccggccagaa caatctgcaa tcccagatca tggatgtggt gaaggaggtc     960
gtccagatcc tgcagcagat gctggcggcg cagaacggcg gcagccagca gtccacctcg    1020
acgcagccga tgtaa                                                     1035
```

The above nucleotide and amino acid sequences are disclosed and further described in U.S. Pat. No. 5,776,889 to Wei et al., which is hereby incorporated by reference in its entirety.

Other embodiments of the present invention include, but are not limited to, use of hypersensitive response elicitor proteins or polypeptides derived from *Erwinia carotovora* and *Erwinia stewartii*. Isolation of an *Erwinia carotovora* hypersensitive response elicitor protein or polypeptide is described in Cui, et al., "The RsmA Mutants of *Erwinia carotovora* subsp. *carotovora* Strain Ecc71 Overexpress hrp-$N_{Ecc}$ and Elicit a Hypersensitive Reaction-like Response in Tobacco Leaves," *MPMI,* 9(7):565-73 (1996), which is hereby incorporated by reference in its entirety. A hypersensitive response elicitor protein or polypeptide of *Erwinia stewartii* is set forth in Ahmad, et al., "Harpin is Not Necessary for the Pathogenicity of *Erwinia stewartii* on Maize," *8th Int'l. Cong. Molec. Plant-Microbe Interact.*, Jul. 14-19, 1996 and Ahmad, et al., "Harpin is Not Necessary for the Pathoge- Necrosis and Acquired Resistance in Tobacco," *Eur. J. Biochem.,* 183:555-63 (1989); Ricci, et al., "Differential Production of Parasiticein, and Elicitor of Necrosis and Resistance in Tobacco, by Isolates of *Phytophthora parasitica*," *Plant Path.* 41:298-307 (1992); Baillreul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance," *Plant J.,* 8(4):551-60 (1995), and Bonnet, et al., "Acquired Resistance Triggered by Elicitors in Tobacco and Other Plants," *Eur. J. Plant Path.,* 102:181-92 (1996), which are hereby incorporated by reference in their entirety.

Another hypersensitive response elicitor protein or polypeptide which can be used in accordance with the present invention is derived from *Clavibacter michiganensis* subsp. *sepedonicus* and is described in U.S. patent application Ser. No. 09/136,625, which is hereby incorporated by reference in its entirety.

Fragments of the above hypersensitive response elicitor proteins or polypeptides as well as fragments of full length elicitors from other pathogens can also be used according to the present invention.

Suitable fragments can be produced by several means. Subclones of the gene encoding a known elicitor protein can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (1989), and Ausubel et al. (ed.), *Current Protocols in Molecular Biology*, John Wiley & Sons (New York, N.Y.) (1999 and preceding editions), which are hereby incorporated by reference in their entirety. The subclones then are expressed in vitro or in vivo in bacterial cells to yield a smaller protein or polypeptide that can be tested for elicitor activity, e.g., using procedures set forth in Wei, Z-M., et al., *Science* 257: 85-88 (1992), which is hereby incorporated by reference in its entirety.

In another approach, based on knowledge of the primary structure of the protein, fragments of the elicitor protein gene may be synthesized using the PCR technique together with specific sets of primers chosen to represent particular portions of the protein. Erlich, H. A., et al., "Recent Advances in the Polymerase Chain Reaction," *Science* 252:1643-51 (1991), which is hereby incorporated by reference in its entirety. These can then be cloned into an appropriate vector for expression of a truncated protein or polypeptide from bacterial cells as described above.

As an alternative, fragments of an elicitor protein can be produced by digestion of a full-length elicitor protein with proteolytic enzymes like chymotrypsin or *Staphylococcus* proteinase A, or trypsin. Different proteolytic enzymes are likely to cleave elicitor proteins at different sites based on the amino acid sequence of the elicitor protein. Some of the fragments that result from proteolysis may be active elicitors of resistance.

Chemical synthesis can also be used to make suitable fragments. Such a synthesis is carried out using known amino acid sequences for the elicitor being produced. Alternatively, subjecting a full length elicitor to high temperatures and pressures will produce fragments. These fragments can then be separated by conventional procedures (e.g., chromatography, SDS-PAGE).

An example of suitable fragments of a hypersensitive response elicitor which elicit a hypersensitive response are fragments of the *Erwinia amylovora* hypersensitive response elicitor protein or polypeptide of SEQ. ID. No. 3. The fragments can be a C-terminal fragment of the amino acid sequence of SEQ. ID. No. 3, an N-terminal fragment of the amino acid sequence of SEQ. ID. No. 3, or an internal fragment of the amino acid sequence of SEQ. ID. No. 3. The C-terminal fragment of the amino acid sequence of SEQ. ID. No. 3 can span amino acids 105 and 403 of SEQ. ID. No. 3. The N-terminal fragment of the amino acid sequence of SEQ. ID. No. 3 can span the following amino acids of SEQ. ID. No. 3: 1 and 98, 1 and 104, 1 and 122, 1 and 168, 1 and 218, 1 and 266, 1 and 342, 1 and 321, and 1 and 372. The internal fragment of the amino acid sequence of SEQ. ID. No. 3 can span the following amino acids of SEQ. ID. No. 3: 76 and 209, 105 and 209, 99 and 209, 137 and 204, 137 and 200, 109 and 204, 109 and 200, 137 and 180, and 105 and 180. DNA molecules encoding these fragments can also be utilized in the chimeric gene of the present invention.

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The hypersensitive response elicitor proteins or polypeptides used in accordance with the present invention are preferably produced in purified form (preferably at least about 80%, more preferably 90%, pure) by conventional techniques. Typically, the protein or polypeptide of the present invention is secreted into the growth medium of recombinant host cells (discussed infra). Alternatively, the protein or polypeptide of the present invention is produced but not secreted into growth medium. In such cases, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to sequential ammonium sulfate precipitation. The fraction containing the hypersensitive response elicitor protein or polypeptide of interest is subjected to gel filtration in an appropriately sized dextran or polyacrylamide column to separate the proteins. If necessary, the protein fraction may be further purified by HPLC.

Other hypersensitive response elicitors can be readily identified by isolating putative protein or polypeptide candidates and testing them for elicitor activity as described, for example, in Wei, Z-M., et al., "Harpin, Elicitor of the Hypersensitive Response Produced by the Plant Pathogen *Erwinia amylovora*," *Science* 257:85-88 (1992), which is hereby incorporated by reference in its entirety. Cell-free preparations from culture supernatants can be tested for elicitor activity (i.e., local necrosis) by using them to infiltrate appropriate plant tissues. Once identified, DNA molecules encoding a hypersensitive response elicitor can be isolated using standard techniques known to those skilled in the art.

DNA molecules encoding other hypersensitive response elicitor proteins or polypeptides can also be identified by determining whether such DNA molecules hybridizes under stringent conditions to a DNA molecule having the nucleotide sequence of SEQ. ID. Nos. 2, 4, 6, 8, 10, or 12. An example of suitable stringency conditions is when hybridization is carried out at a temperature of about 37° C. using a hybridization medium that includes 0.9M sodium citrate ("SSC") buffer, followed by washing with 0.2×SSC buffer at 37° C. Higher stringency can readily be attained by increasing the temperature for either hybridization or washing conditions or increasing the sodium concentration of the hybridization or wash medium. Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions are typically performed at or below stringency. Exemplary high stringency conditions include carrying out hybridization at a temperature of about 42° C. to about 65° C. for up to about 20 hours in a hybridization medium containing 1M NaCl, 50 mM Tris-HCl, pH 7.4, 10 mM EDTA, 0.1% sodium dodecyl sulfate (SDS), 0.2% ficoll, 0.2% polyvinylpyrrolidone, 0.2% bovine serum albumin, and 50 μg/ml *E. coli* DNA, followed by washing carried out at between about 42° C. to about 65° C. in a 0.2×SSC buffer.

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7-9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

Because it is desirable for recombinant host cells to secrete the hypersensitive response elicitor protein or polypeptide, it is preferable that the host cell also be transformed with a type III secretion system in accordance with Ham et al., "A Cloned *Erwinia chrysanthemi* Hrp (Type III Protein Secretion) System Functions in *Escherichia coli* to Deliver *Pseudomonas*

*syringae* Avr Signals to Plant Cells and Secrete Avr Proteins in Culture," *Microbiol.* 95:10206-10211 (1998), which is hereby incorporated by reference in its entirety.

Isolation of the hypersensitive response elicitor protein or polypeptide from the host cell or growth medium can be carried out as described above.

The methods of the present invention can be performed by treating the fruit or vegetable either prior to or after harvest of the fruit or vegetable.

Suitable preharvest application methods include, without limitation, high or low pressure spraying of the entire plant and fruits. Suitable postharvest application methods include, without limitation, low or high pressure spraying, coating, or immersion. Other suitable application procedures (both pre-harvest and postharvest) can be envisioned by those skilled in the art provided they are able to effect contact of the hypersensitive response elicitor polypeptide or protein with the fruit or vegetable. Once treated, the fruits or vegetables can be handled, packed, shipped, and processed using conventional procedures to deliver the produce to processing plants or end-consumers.

The hypersensitive response elicitor polypeptide or protein can be applied to fruits or vegetables in accordance with the present invention alone or in a mixture with other materials. Alternatively, the hypersensitive response elicitor polypeptide or protein can be applied separately to fruits or vegetables with other materials being applied at different times.

A composition suitable for treating fruits or vegetables in accordance with the application embodiment of the present invention contains an isolated hypersensitive response elicitor polypeptide or protein in a carrier. Suitable carriers include water, aqueous solutions, slurries, or dry powders. The composition preferably contains greater than about 500 nM hypersensitive response elicitor polypeptide or protein, although greater or lesser amounts of the hypersensitive response elicitor polypeptide or protein depending on the rate of composition application and efficacy of different hypersensitive response elicitor proteins or polypeptides.

Although not required, this composition may contain additional additives including fertilizer, insecticide, fungicide, nematacide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and ripening agents. These materials can be used either to facilitate the process of the present invention or to provide additive benefits to inhibit postharvest disease and desiccation.

As indicated above, one embodiment of the present invention involves treating fruits or vegetables with an isolated hypersensitive response elicitor protein or polypeptide. The hypersensitive response elicitor protein or polypeptide can be isolated from its natural source (e.g., *Erwinia amylovora*, *Pseudomonas syringae*, etc.) or from recombinant source transformed with a DNA molecule encoding the protein or polypeptide.

Another aspect of the present invention relates to a DNA construct as well as host cells, expression systems, and transgenic plants which contain the heterologous DNA construct.

The DNA construct includes a DNA molecule encoding a hypersensitive response elicitor protein or polypeptide, a plant-expressible promoter operably coupled 5' to the DNA molecule and which is effective to transcribe the DNA molecule in fruit or vegetable tissue, and a 3' regulatory region operably coupled to the DNA molecule. Expression of the DNA molecule in fruit or vegetable tissue imparts to a fruit or vegetable resistance against postharvest disease or desiccation.

Expression of such heterologous DNA molecules requires a suitable promoter which is operable in plant tissues. In some embodiments of the present invention, it may be desirable for the heterologous DNA molecule to be expressed in many, if not all, tissues. Such promoters yield constitutive expression of coding sequences under their regulatory control. Exemplary constitutive promoters include, without limitation, the nopaline synthase promoter (Fraley et al., *Proc. Natl. Acad. Sci. USA* 80:4803-4807 (1983), which is hereby incorporated by reference in its entirety) and the cauliflower mosaic virus 35S promoter (O'Dell et al., "Identification of DNA Sequences Required for Activity of the Cauliflower Mosaic Virus 35S Promoter," *Nature,* 313(6005):810-812 (1985), which is hereby incorporated by reference in its entirety).

While constitutive expression is generally suitable for expression of the DNA molecule, it should be apparent to those of skill in the art that temporally or tissue regulated expression may also be desirable, in which case any regulated promoter can be selected to achieve the desired expression. Typically, the temporally or tissue regulated promoters will be used in connection with the DNA molecule that are expressed at only certain stages of development or only in certain tissues.

In another embodiment of the present invention, expression of the heterologous DNA molecule is directed in a tissue-specific manner or environmentally-regulated manner (i.e., inducible promoters). Tissue-specific promoters under developmental control include promoters that initiate transcription only in certain tissues.

For example, the E4 and E8 promoters of tomato have been used to direct fruit-specific expression of a heterologous DNA sequence in transgenic tomato plants (Cordes et al., *Plant Cell* 1:1025-1034 (1989); Deikman et al., *EMBO J.* 7:3315-3320 (1988); and Della Penna et al., *Proc. Natl. Acad. Sci. USA* 83:6420-6424 (1986), which are hereby incorporated by reference in their entirety). Another fruit-specific promoter is the PG promoter (Bird et al., *Plant Molec. Biol.* 11:651-662 (1988), which is hereby incorporated by reference in its entirety). Another tissue-specific promoter is the AP2 promoter from the ovule-specific BEL1 gene promoter described in Reiser et al., *Cell* 83:735-742 (1995), which is hereby incorporated by reference in its entirety.

Promoters useful for expression in seed tissues include, without limitation, the promoters from genes encoding seed storage proteins, such as napin, cruciferin, phaseolin, and the like (see U.S. Pat. No. 5,420,034 to Kridl et al., which is hereby incorporated by reference in its entirety). Other suitable promoters include those from genes encoding embryonic storage proteins.

Promoters useful for expression in leaf tissue include the Rubisco small subunit promoter.

Promoters useful for expression in tubers, particularly potato tubers, include the patatin promoter.

Examples of environmental conditions that may affect transcription by inducible promoters include anaerobic conditions, elevated temperature, or the presence of light. In some plants, it may also be desirable to use promoters which are responsive to pathogen infiltration or stress. For example, it may be desirable to limit expression of the protein or polypeptide in response to infection by a particular pathogen of the plant. One example of a pathogen-inducible promoter is the gst1 promoter from potato, which is described in U.S. Pat. Nos. 5,750,874 and 5,723,760 to Strittmayer et al., which are hereby incorporated by reference in their entirety.

Expression of the DNA molecule in isolated plant cells or tissue or whole plants also utilizes appropriate transcription termination and polyadenylation of mRNA. Any 3' regulatory region suitable for use in plant cells or tissue can be operably linked to the first and second DNA molecules. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l. Acad. Sci. USA*, 80:4803-4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature*, 313(6005):810-812 (1985), which is hereby incorporated by reference in its entirety).

The promoter and a 3' regulatory region can readily be ligated to the DNA molecule using well known molecular cloning techniques described in Sambrook et al., *Molecular Cloning: A Laboratory Manual*, Second Edition, Cold Spring Harbor Press, NY (1989), which is hereby incorporated by reference in its entirety.

One approach to transforming plant cells with a DNA molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford, et al., which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Another method of introducing the DNA molecule into plant cells is fusion of protoplasts with other entities, either minicells, cells, lysosomes, or other fusible lipid-surfaced bodies that contain the DNA molecule. Fraley, et al., *Proc. Natl. Acad. Sci. USA*, 79:1859-63 (1982), which is hereby incorporated by reference in its entirety.

The DNA molecule may also be introduced into the plant cells by electroporation. Fromm, et al., *Proc. Natl. Acad. Sci. USA*, 82:5824 (1985), which is hereby incorporated by reference in its entirety. In this technique, plant protoplasts are electroporated in the presence of plasmids containing the DNA molecule. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *Agrobacterium rhizogenes* previously transformed with the DNA molecule. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25-28° C.

*Agrobacterium* is a representative genus of the Gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences such as a DNA molecule a hypersensitive response elicitor protein or polypeptide can be introduced into appropriate plant cells by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. Schell, J., *Science*, 237:1176-83 (1987), which is hereby incorporated by reference in its entirety.

Plant tissue suitable for transformation include leaf tissue, root tissue, meristems, zygotic and somatic embryos, and anthers.

After transformation, the transformed plant cells can be selected and regenerated.

Preferably, transformed cells are first identified using, e.g., a selection marker simultaneously introduced into the host cells along with the DNA molecule of the present invention. Suitable selection markers include, without limitation, markers coding for antibiotic resistance, such as kanamycin resistance (Fraley, et al., *Proc. Natl. Acad. Sci. USA*, 80:4803-4807 (1983), which is hereby incorporated by reference in its entirety). A number of antibiotic-resistance markers are known in the art and other are continually being identified. Any known antibiotic-resistance marker can be used to transform and select transformed host cells in accordance with the present invention. Cells or tissues are grown on a selection media containing an antibiotic, whereby generally only those transformants expressing the antibiotic resistance marker continue to grow.

Once a recombinant plant cell or tissue has been obtained, it is possible to regenerate a full-grown plant therefrom. Thus, another aspect of the present invention relates to a transgenic plant that includes a heterologous DNA molecule encoding a hypersensitive response elicitor protein or polypeptide, wherein the heterologous DNA molecule is under control or a promoter that induces transcription of the DNA molecule fruit or vegetable tissues. Preferably, the DNA molecule is stably inserted into the genome of the transgenic plant of the present invention.

Plant regeneration from cultured protoplasts is described in Evans, et al., *Handbook of Plant Cell Cultures, Vol. 1*: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference in their entirety.

It is known that practically all plants can be regenerated from cultured cells or tissues, including both monocots and dicots.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the DNA molecule encoding the hypersensitive response elicitor protein or polypeptide is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field.

With regard to the use of the hypersensitive response elicitor protein or polypeptide in imparting postharvest disease resistance, absolute immunity against infection may not be conferred, but the severity of the disease can be reduced and symptom development can be delayed. Lesion number, lesion size, and extent of sporulation of fungal pathogens are all decreased. This method of controlling postharvest disease has the potential for controlling previously untreatable diseases and avoiding the use of infectious agents or environmentally harmful materials.

With respect to desiccation, complete protection against desiccation may not be conferred, but the severity of desiccation can be reduced. Desiccation protection inevitably will depend, at least to some extent, on other conditions such as storage temperatures, light exposure, etc. However, this method of controlling desiccation has the potential for eliminating some other treatments (i.e., use of coating waxes) which may contribute to reduced costs or, at least, substantially no increase in costs.

The methods of the present invention can be used to control a number of postharvest diseases caused by a variety of pathogens. These postharvest diseases and the causative agents which can be treated according to the present invention include, without limitation, the following: Penicillium (e.g., Penicillium digitatum), Botrytis (e.g., Botrytis cinereaon), Phytophthora (e.g., Phytophthora citrophthora), and Erwinia (e.g. Erwinia carotovora).

A further aspect of the present invention relates to a method of enhancing the longevity of fruit or vegetable ripeness.

According to one embodiment, this aspect of the present invention is carried out by treating a fruit or vegetable with a hypersensitive response elicitor protein or polypeptide under conditions effective to enhance the longevity of fruit or vegetable ripeness. Preferably, as noted above, the hypersensitive response elicitor protein or polypeptide is in isolated form. Treating of the fruit or vegetable can be performed either prior to harvest after harvest of the fruit or vegetable, using the techniques described above.

According to another embodiment, this aspect of the present invention is carried out by providing a transgenic plant or plant seed transformed with a DNA molecule encoding a hypersensitive response elicitor polypeptide or protein and then growing the transgenic plant or transgenic plant produced from the transgenic plant seed under conditions effective to enhance the longevity of fruit or vegetable ripeness in a fruit or vegetable harvested from the transgenic plant. This aspect of the present invention may further include applying the hypersensitive response elicitor polypeptide or protein to the fruit or vegetable to enhance the longevity of fruit or vegetable ripeness. Treating of the fruit or vegetable can be performed either prior to harvest or after harvest of the fruit or vegetable, using the techniques described above.

The methods of the present invention can be utilized to treat a wide variety of fruits and vegetables to control postharvest disease or desiccation as well as enhance the longevity of fruit or vegetable ripeness. Fruits and vegetables which can be treated include any edible plant product, particularly those from traditional crop plants, such as seed, root, tuber, stem, leaf, flower, and fruit. Exemplary transgenic fruit plants and fruits that can be treated include, without limitation, apple, pear, peach, nectarine, apricot, plum, cherry, olive, melon, citrus, grape, strawberry, raspberry, blueberry, currant, pineapple, papaya, guava, banana, and kiwi. Exemplary transgenic vegetable plants and vegetables that can be treated include, without limitation, asparagus, potato, sweet potato, bean, pea, chicory, lettuce, parsley, basil, endive, cabbage, brussel sprout, beet, parsnip, turnip, cauliflower, broccoli, spinach, onion, garlic, eggplant, pepper, celery, leek, radish, carrot, squash, pumpkin, zucchini, cucumber, soybean, tobacco, tomato, sorghum, rhubarb, and sugarcane. Exemplary transgenic grain plants and grain products which can be treated include, without limitation, alfalfa, rice, wheat, barley, corn, and rye.

EXAMPLES

The following examples are provided to illustrate embodiments of the present invention but are by no means intended to limit its scope.

As used in the following Examples, Messenger® refers to a product available from Eden Bioscience Corporation (Bothell, Wash.), which contains 3% by weight of harpin$_{Ea}$ as the active ingredient and 97% by weight inert ingredients. Harpin$_{Ea}$, is one type of hypersensitive response elicitor protein from Erwinia amylovora, identified herein by SEQ. ID. No. 3.

Example 1

Effect of Treating Orange Fruits with Messenger® on Postharvest Orange Storage

On day 0, Fall-GLO orange fruits were treated by spraying Messenger® solution (ca. 15 ug/ml) or buffer solution (5 mM KPO$_4$, pH 6.8) on the surface of fruits in a 22° C. greenhouse. The Messenger® or buffer solutions on oranges were then dried by air, and the treated oranges were marked, mixed together, and put into a plastic container (ClearView 66 Qt/63 L made by Sterilite Corporation). The container with treated oranges was then put into a 18° C. growth chamber for storage. On day 7, orange fruits were inoculated with Penicillium digitatum and Botrytis cinereaon by spraying a 10$^5$ cfu/ml suspension on the surface of orange fruit. The above procedure was performed on 40 orange fruits per treatment.

Measurements of disease were conducted on days 20, 24, and 26 following treatment with Messenger® or buffer solution. Grades 0-5 indicate different disease scales—Grade 0: No symptoms; Grade 1: ⅕ an individual fruit has disease symptoms; Grade 2: ⅖ an individual fruit has disease symptoms; Grade 3: ⅗ an individual fruit has disease symptoms; Grade 4: ⅘ an individual fruit has disease symptoms; Grade 5: whole fruit has disease symptoms. The results of these treatments are set forth in Table 1 below.

TABLE 1

Reduction of Disease Index in Oranges

| Sample | Days After Treatment | Grade | | | | | | Index | Efficacy | T-test | |
| --- | --- | --- | --- | --- | --- | --- | --- | --- | --- | --- | --- |
| | | 0 | 1 | 2 | 3 | 4 | 5 | | | $p < 0.05$ | $p < 0.01$ |
| Messenger ® | 20 | 33 | 3 | 1 | 0 | 2 | 1 | 0.09 | 58.14% | yes | yes |
| Buffer | 20 | 23 | 8 | 0 | 2 | 6 | 1 | 0.22 | n/a | — | — |
| Messenger ® | 24 | 25 | 2 | 6 | 4 | 1 | 2 | 0.20 | 45.21% | yes | yes |
| Buffer | 24 | 16 | 7 | 3 | 3 | 4 | 7 | 0.37 | n/a | — | — |
| Messenger ® | 26 | 19 | 4 | 6 | 4 | 5 | 2 | 0.29 | 36.96% | yes | yes |
| Buffer | 26 | 16 | 3 | 3 | 0 | 7 | 11 | 0.46 | n/a | — | — |

The data listed in Table 1 above shows that the Messenger® was more effective than buffer as a fruit spray treatment in reducing disease index for *Penicillium digitatum* and *Botrytis cinereaon* and providing longer storage life. Messenger® treatment can reduce orange disease about 58.14% at 21 days, about 45.21% at 25 days, and 36.97% at 27 days after spraying treatment and 18° C. storage conditions. T-test shows that there are statistically significant differences at both 95% and 99% confidence levels for the results obtained from Messenger Treatment® and buffer treatment.

Example 2

Effect of Treating Tomato (Hot House) Fruits with Messenger® on Postharvest Tomato Storage On day 0, Hot House tomato fruits were treated by spraying Messenger® solution (ca. 15 ug/ml) or buffer solution (5 mM $KPO_4$, pH 6.8) on the surface of fruits in a 22° C. greenhouse. The Messenger® or buffer solutions on tomatoes were then dried by air, and the treated tomatoes were marked, mixed together, and put into a plastic container (ClearView 66 Qt/63 L made by Sterilite Corporation). The container with treated tomatoes was then put into 18° C. growth chamber for storage. On day 7, tomatoes were inoculated with *Penicillium digitatum* and *Botrytis cinereaon* by spraying a $10^5$ cfu/ml suspension on the surface of tomato fruit. The above procedure was performed on 15 tomatoes fruits per treatment.

Measurements of disease were conducted on days 21 and 27 following treatment with Messenger® or buffer solution. Grades are indicated according to the criteria set forth in Example 1. The results of these treatments are set forth in Table 2 below.

The data listed in Table 2 above shows that the Messenger® was more effective than buffer as a fruit spray treatment in reducing disease index for *Penicillium digitatum* and *Botrytis cinereaon* and providing longer storage life. Messenger® treatment can reduce tomato disease about 58.70% at 21 days and about 30.19% at 27 days after spraying treatment and 18° C. storage conditions. T-test shows that there are statistically significant differences at both 95% and 99% confidence levels for the results obtained from Messenger Treatment® and buffer treatment.

Example 3

Effect of Treating Grape Fruits with Messenger® on Postharvest Grape Storage

On day 0, Red G. Grape fruits were treated by spraying Messenger® solution (ca. 15 ug/ml) or buffer solution (5 mM $KPO_4$, pH 6.8) on the surface of fruits in a 22° C. greenhouse. The Messenger® or buffer solutions on grapes were then dried by air, and the treated grapes were marked, mixed together, and put into a plastic container (ClearView 66 Qt/63 L made by Sterilite Corporation). The container with treated grapes was then put into a 18° C. growth chamber for storage. On day 7, grapes were inoculated with *Penicillium digitatum* and *Botrytis cinereaon* by spraying a $10^5$ cfu/ml suspension on the surface of grape fruit. The above procedure was performed on about 3700 g of grape fruits per treatment.

Measurements of disease were conducted on days 14 and 21 following treatment with Messenger® or buffer solution. Grades are indicated according to the criteria set forth in Example 1. The results of these treatments are set forth in Table 3 below.

TABLE 2

Reduction of Disease Index in Tomatoes

| Sample | Days After Treatment | Grade | | | | | | Index | Efficacy | T-test | |
| --- | --- | --- | --- | --- | --- | --- | --- | --- | --- | --- | --- |
| | | 0 | 1 | 2 | 3 | 4 | 5 | | | $p < 0.05$ | $p < 0.01$ |
| Messenger ® | 21 | 7 | 2 | 2 | 3 | 1 | 0 | 0.25 | 58.70% | yes | yes |
| Buffer | 21 | 3 | 1 | 2 | 1 | 2 | 6 | 0.61 | n/a | — | — |
| Messenger ® | 27 | 2 | 2 | 4 | 3 | 2 | 2 | 0.49 | 30.19% | yes | yes |
| Buffer | 27 | 1 | 1 | 2 | 2 | 3 | 6 | 0.71 | n/a | — | — |

TABLE 3

Reduction of Disease Index in Grapes

| Sample | Days After Treatment | Grade | | | | | | Index | Efficacy | T-test p < 0.05 | p < 0.01 |
|---|---|---|---|---|---|---|---|---|---|---|---|
| | | 0 | 1 | 2 | 3 | 4 | 5 | | | | |
| Messenger® | 14 | 225 | 99 | 42 | 39 | 21 | 13 | 0.20 | 45.65% | yes | yes |
| Buffer | 14 | 98 | 130 | 91 | 52 | 38 | 48 | 0.38 | n/a | — | — |
| Messenger® | 21 | 66 | 83 | 126 | 98 | 39 | 27 | 0.42 | 39.35% | yes | yes |
| Buffer | 21 | 18 | 36 | 64 | 72 | 119 | 137 | 0.69 | n/a | — | — |

The data listed in Table 3 above shows that the Messenger® was more effective than buffer as a fruit spray treatment in reducing disease index for *Penicillium digitatum* and *Botrytis cinereaon* and providing longer storage life. Messenger® treatment can reduce grape disease by about 45.65% at 14 days and about 39.35% at 21 days after spraying treatment and 18° C. storage conditions. T-test shows that there are statistically significant differences at both 95% and 99% confidence levels for the results obtained from Messenger Treatment® and buffer treatment.

Example 4

Effect of Treating Grapefruit Fruits with Messenger® on Postharvest Grapefruit Storage On day 0, FL 33935 grapefruit fruits were treated by spraying Messenger® solution (ca. 15 ug/ml) or buffer solution (5 mM $KPO_4$, pH 6.8) on the surface of fruits in a 22° C. greenhouse. The Messenger® or buffer solutions on grapefruits were then dried by air, and the treated grapefruits were marked, mixed together, and put into a plastic container (Clear View 66 Qt/63 L made by Sterilite Corporation). The container with treated grapefruit fruits was then put into a 18° C. growth chamber for storage. On day 7, grapefruit fruits were inoculated with *Phytophthora citrophthora* by spraying a $10^5$ cfu/ml suspension on the surface of grapefruit fruit. The above procedure was performed on 6 grapefruit fruits per treatment.

Measurements of disease were conducted on days 87, 97, 103, and 111 following treatment with Messenger® or buffer solution. Grades are indicated according to the criteria set forth in Example 1. The results of these treatments are set forth in Table 4 below.

The data listed in Table 4 above shows that the Messenger® was more effective than buffer as a fruit spray treatment in reducing disease index for *Phytophthora citrophthora* and providing longer storage life. Messenger® treatment can reduce grapefruit disease by about 75.00% at 87 days, about 50.00% at 97 days, about 28.57% at 103 days, and about 33.33% at 111 days after spraying treatment and 18° C. storage conditions. T-test shows that there are statistically significant differences at both 95% and 99% confidence levels for the results obtained from Messenger Treatment® and buffer treatment.

Example 5

Effect of Treating Apple (Fuji) Fruits with Messenger® on Postharvest Apple Storage On day 0, Fuji apple fruits were treated by spraying Messenger® solution (ca. 15 ug/ml) or buffer solution (5 mM $KPO_4$, pH 6.8) on the surface of fruits in a 22° C. greenhouse. The Messenger® or buffer solutions on apples were then dried by air, and the treated apples were marked, mixed together, and put into a plastic container (Clear View 66 Qt/63 L made by Sterilite Corporation). The container with treated apples was then put into a 18° C. growth chamber for storage. On day 7, apples were inoculated with *Penicillium digitatum* and *Phytophthora citrophora* by spraying a $10^5$ cfu/ml suspension on the surface of apples. The above procedure was performed on 20 apples per treatment.

Measurements of disease were conducted on days 50, 61, 70, 78, and 85 following treatment with Messenger® or buffer solution. Grades are indicated according to the criteria set forth in Example 1. The results of these treatments are set forth in Table 5 below.

TABLE 4

Reduction of Disease Index in Grapefruits

| Sample | Days After Treatment | Grade | | | | | | Index | Efficacy | T-test p < 0.05 | p < 0.01 |
|---|---|---|---|---|---|---|---|---|---|---|---|
| | | 0 | 1 | 2 | 3 | 4 | 5 | | | | |
| Messenger® | 87 | 5 | 1 | 0 | 0 | 0 | 0 | 0.03 | 75.00% | yes | yes |
| Buffer | 87 | 4 | 1 | 0 | 1 | 0 | 0 | 0.13 | n/a | — | — |
| Messenger® | 97 | 5 | 0 | 0 | 1 | 0 | 0 | 0.10 | 50.00% | yes | yes |
| Buffer | 97 | 4 | 0 | 1 | 0 | 1 | 0 | 0.20 | n/a | — | — |
| Messenger® | 103 | 4 | 1 | 0 | 0 | 1 | 0 | 0.17 | 28.57% | yes | yes |
| Buffer | 103 | 3 | 2 | 0 | 0 | 0 | 1 | 0.23 | n/a | — | — |
| Messenger® | 111 | 4 | 1 | 0 | 0 | 0 | 1 | 0.20 | 33.33% | yes | yes |
| Buffer | 111 | 3 | 1 | 0 | 1 | 0 | 1 | 0.30 | n/a | — | — |

TABLE 5

Reduction of Disease Index in Apples

| Sample | Days After Treatment | Grade | | | | | | Index | Efficacy | T-test | |
|---|---|---|---|---|---|---|---|---|---|---|---|
| | | 0 | 1 | 2 | 3 | 4 | 5 | | | $p < 0.05$ | $p < 0.01$ |
| Messenger® | 50 | 20 | 0 | 0 | 0 | 0 | 0 | 0.00 | 100.00% | yes | yes |
| Buffer | 50 | 18 | 1 | 1 | 0 | 0 | 0 | 0.03 | n/a | — | — |
| Messenger® | 61 | 19 | 1 | 0 | 0 | 0 | 0 | 0.01 | 88.89% | yes | yes |
| Buffer | 61 | 16 | 2 | 1 | 0 | 0 | 1 | 0.09 | n/a | — | — |
| Messenger® | 70 | 18 | 0 | 2 | 0 | 0 | 0 | 0.04 | 71.43% | yes | yes |
| Buffer | 70 | 14 | 2 | 2 | 1 | 0 | 1 | 0.14 | n/a | — | — |
| Messenger® | 78 | 15 | 2 | 3 | 0 | 0 | 0 | 0.08 | 57.89% | yes | yes |
| Buffer | 78 | 13 | 2 | 2 | 1 | 0 | 2 | 0.19 | n/a | — | — |
| Messenger® | 85 | 13 | 3 | 1 | 1 | 2 | 0 | 0.16 | 40.74% | yes | yes |
| Buffer | 85 | 10 | 5 | 0 | 0 | 3 | 2 | 0.27 | n/a | — | — |

The data listed in Table 5 above shows that the Messenger® was more effective than buffer as a fruit spray treatment in reducing disease index for *Penicillium digitatum* and *Phytophthora citrophora* and providing longer storage life. Messenger® treatment can reduce apple disease by about 100.00% at 51 days, 88.89% at 61 days, 71.43% at 70 days, 57.89% at 78 days, and 40.74% at 85 days after spraying treatment and 18° C. storage conditions. T-test shows that there are statistically significant differences at both 95% and 99% confidence levels for the results obtained from Messenger Treatment® and buffer treatment.

Example 6

Effect of Treating Apple (Granny Smith) Fruits with Messenger® on Postharvest Apple Storage On day 0, Granny Smith apple fruits were treated by spraying Messenger® solution (ca. 15 ug/ml) or buffer solution (5 mM $KPO_4$, pH 6.8) on the surface of fruits in a 22° C. greenhouse. The Messenger® or buffer solutions on apples were then dried by air, and the treated apples were marked, mixed together, and put into a plastic container (Clear View 66 Qt/63 L made by Sterilite Corporation). The container with treated apples was then put into a 18° C. growth chamber for storage. On day 7, apples were inoculated with *Penicillium digitatum* and *Phytophthora citrophora* by spraying a $10^5$ cfu/ml suspension on the surface of apples. The above procedure was performed on 20 apples per treatment.

Measurements of disease were conducted on days 50, 61, 70, 78, and 85 following treatment with Messenger® or buffer solution. Grades are indicated according to the criteria set forth in Example 1. The results of these treatments are set forth in Table 6 below.

The data listed in Table 6 above shows that the Messenger® was more effective than buffer as a fruit spray treatment in reducing disease index for *Penicillium digitatum* and *Phytophthora citrophora* and providing longer storage life. Messenger® treatment can reduce apple disease by about 100.00% at 51 days, 50.00% at 61 days, 36.00% at 70 days, 32.14% at 78 days, and 23.08% at 85 days after spraying treatment and 18° C. storage conditions. T-test shows that there are statistically significant differences at both 95% and 99% confidence levels for the results obtained from Messenger Treatment® and buffer treatment.

Example 7

Effect of Treating Tomato Fruits with Messenger® on Postharvest Tomato Storage

On day 0, tomato fruits were treated by spraying Messenger® solution (ca. 15 ug/ml) or buffer solution (5 mM $KPO_4$, pH 6.8) on the surface of fruits in a 22° C. greenhouse. After the Messenger® or buffer solutions on tomatoes were dried by air, the treated tomatoes were marked, mixed together, and put into a plastic container (Clear View 66 Qt/63 L made by Sterilite Corporation). The container with treated tomatoes was then put into a 18° C. growth chamber for storage. On day 7, tomatoes were inoculated with *Penicillium digitatum* and *Botrytis cinereao*n by spraying a $10^5$ cfu/ml suspension on the surface of tomatoes. The above procedure was performed on 44 tomatoes per treatment.

Measurements of disease were conducted on days 18, 27, 35, and 42 following treatment with Messenger® or buffer solution. Grades are indicated according to the criteria set forth in Example 1. The results of these treatments are set forth in Table 7 below.

TABLE 6

Reduction of Disease Index in Apples

| Sample | Days After Treatment | Grade | | | | | | Index | Efficacy | T-test | |
|---|---|---|---|---|---|---|---|---|---|---|---|
| | | 0 | 1 | 2 | 3 | 4 | 5 | | | $p < 0.05$ | $p < 0.01$ |
| Messenger® | 50 | 20 | 0 | 0 | 0 | 0 | 0 | 00.00 | 100.00% | yes | yes |
| Buffer | 50 | 19 | 1 | 0 | 0 | 0 | 0 | 0.01 | n/a | — | — |
| Messenger® | 61 | 13 | 5 | 2 | 0 | 0 | 0 | 0.09 | 50.00% | yes | yes |
| Buffer | 61 | 7 | 9 | 3 | 1 | 0 | 0 | 0.18 | n/a | — | — |
| Messenger® | 70 | 7 | 10 | 3 | 0 | 0 | 0 | 0.16 | 36.00% | yes | yes |
| Buffer | 70 | 2 | 12 | 5 | 1 | 0 | 0 | 0.25 | n/a | — | — |
| Messenger® | 78 | 6 | 10 | 3 | 1 | 0 | 0 | 0.19 | 32.14% | yes | yes |
| Buffer | 78 | 2 | 11 | 5 | 1 | 1 | 0 | 0.28 | n/a | — | — |
| Messenger® | 85 | 7 | 9 | 2 | 1 | 1 | 0 | 0.20 | 23.08 | yes | yes |
| Buffer | 85 | 4 | 10 | 4 | 1 | 0 | 1 | | n/a | — | — |

TABLE 7

Reduction of Disease Index in Tomatoes

| Sample | Days After Treatment | Grade 0 | 1 | 2 | 3 | 4 | 5 | Index | Efficacy | T-test p < 0.05 | p < 0.01 |
|---|---|---|---|---|---|---|---|---|---|---|---|
| Messenger ® | 18 | 21 | 18 | 5 | 0 | 0 | 0 | 0.13 | 37.78% | yes | yes |
| Buffer | 18 | 11 | 21 | 12 | 0 | 0 | 0 | 0.20 | n/a | — | — |
| Messenger ® | 27 | 16 | 18 | 9 | 1 | 0 | 0 | 0.18 | 25.00% | yes | yes |
| Buffer | 27 | 8 | 24 | 8 | 4 | 0 | 0 | 0.24 | n/a | — | — |
| Messenger ® | 35 | 7 | 14 | 13 | 10 | 0 | 0 | 0.32 | 16.67% | yes | yes |
| Buffer | 35 | 1 | 16 | 15 | 10 | 2 | 0 | 0.38 | n/a | — | — |
| Messenger ® | 42 | 1 | 10 | 9 | 12 | 9 | 3 | 0.52 | 12.88% | yes | yes |
| Buffer | 42 | 0 | 3 | 15 | 10 | 11 | 5 | 0.60 | n/a | — | — |

The data listed in Table 7 above shows that the Messenger® was more effective than buffer as a fruit spray treatment in reducing disease index for *Penicillium digitatum* and *Botrytis cinereaon* and providing longer storage life. Messenger® treatment can reduce tomato disease by about 37.78% at 18 days, 25.00% at 27 days, 16.67% at 35 days, and 12.88% at 42 days after spraying treatment and 18° C. storage conditions. T-test shows that there are statistically significant differences at both 95% and 99% confidence levels for the results obtained from Messenger® treatment and buffer treatment.

Example 8

Effect of Preharvest and Postharvest Messenger® Treatments on Tomato (Sanibel) Fruit Postharvest Storage Plots of red and green Sanibel variety tomatoes were grown under either standard conditions or full Messenger® treatment over the course of the growing season. The standard conditions, also known as grower's standard, included fungicide treatment sprayed every seven days after transplanting using primarily fungicides containing copper-based active ingredients. The Messenger® treatment included six sprays at rate of 2.2 oz of the product per acre.

Red and green fruits were harvested from both the Messengers treated and grower standard plots. It was noted that green tomatoes from the grower standard treatment plots were smaller (i.e. less mature) then green tomatoes from the messenger treated plants.

Harvested fruits were treated as follows:
(1) Fruits from Messenger® treated plots were further treated with Messenger® after harvest;
(2) Fruits from standard plots were treated with Messenger® after harvest;
(3) Fruits from Messenger® treated plots received no additional treatment following harvest; and
(4) Fruits from standard plots received no additional treatment following harvest.

Postharvest treatment of fruits from groups (1) and (2) was carried out by spraying with Messenger® at a rate of 20 ppm harpin$_{Ea}$ concentration using a backpack-sprayer at about 30 p.s.i. The fruit were rolled during application to assure full coverage of the spray. The postharvest treated tomatoes were allowed to air dry and then tomatoes from groups (1)-(4) were marked and mixed together in storage in a single layer. Storage temperatures ranged from about 18 to 32° C. and light intervals were approximately 12 hours of light and darkness. Tomatoes were checked daily for rot and desiccation for a total of 31 days after harvest. The results are shown in Table 8 below.

TABLE 8

Affect of Preharvest and Postharvest Treatment on Rot and Desiccation

| Group | Ripeness | No. Fruit | Days After Harvest 14 | 19 | 21 | 22 | 23 | 25 | 31 | No. Desiccated | % Marketable |
|---|---|---|---|---|---|---|---|---|---|---|---|
| (1) Pre/Postharvest Messenger ® | Red | 5 | 0 | 0 | 0 | 1 | 1 | 1 | 2 | 0 | 60% |
|  | Green | 4 | 0 | 0 | 0 | 0 | 0 | 0 | 0 | 0 | 100% |
| (2) Postharvest Messenger ® Only | Red | 5 | 0 | 0 | 0 | 0 | 0 | 0 | 0 | 4 | 20% |
|  | Green | 4 | 0 | 0 | 0 | 0 | 0 | 0 | 0 | 1 | 75% |
| (3) Preharvest Messenger ® Only | Red | 5 | 0 | 0 | 0 | 0 | 0 | 0 | 2 | 0 | 60% |
|  | Green | 5 | 0 | 0 | 0 | 0 | 0 | 0 | 0 | 0 | 100% |
| (4) No Messenger ® | Red | 5 | 1 | 3 | 1 | 5 | 5 | 5 | 5 | 0 | 0% |
|  | Green | 5 | 0 | 0 | 0 | 0 | 0 | 0 | 0 | 1 | 80% |

The red tomatoes from group (4) all rotted by day 21. In contrast, all red tomatoes which received some form of Messengers treatment showed reduced rate of decay and rot. Near the end of the trial a number of tomatoes were observed to have desiccated, exhibiting shriveled skins but no rot. These were included as non-marketable. These results are suggestive that both preharvest and postharvest Messenger® treatments can reduce the level of rotting and desiccation, thereby extending fresh storage time.

Example 9

Effect of Messenger on Post Harvested Maturity and Fruit Decay on Tomato During Ambient Storage The tomatoes were grown under either standard conditions (identified in Example 8) or full Messenger® treatment over the course of the growing season (identified in Example 8) and then hand picked at the time of commercial harvest. Mature green fruit of uniform size (5/6) were collected throughout the field in four replicate samples of 25 fruit per sample, placed directly into fruit bags and transported to a laboratory facility for postharvest treatment and/or analysis. Three different treatment regimen were examined as follows:
(1) Fruits from Messenger® treated plots received no additional treatment following harvest;
(2) Fruits from standard plots were treated with Messenger® after harvest;
(3) Fruits from standard plots received no additional treatment following harvest.

Postharvest treatment of fruits from group (2) was carried out by dipping the fruit in a Messenger® solution (20 ppm harpin$_{Ea}$). The postharvest treated tomatoes were allowed to air dry and then tomatoes from groups (1)-(3) were marked and mixed together in tomato crates for storage. Storage temperatures ranged from about 23 to 26° C. (75-80° F.). The tomatoes were then rated for color development and decay over time using the rating scale below.

| Grade | Description |
|---|---|
| 1 | Mature Green: When fruit cut in half, no seeds cut; fruit entirely green with no color break; |
| 2 | Pink: Initial sign of color break noticed on some areas of fruit; these areas are usually pink; |
| 3 | Pink/Red: Intermediate ripening: Fruit is not total red; some pink still remains; |
| 4 | Red: Fruit totally red in color; |
| 5 | Decay: Some areas of the fruit beginning to break down from decay. |

The results of this test are summarized in Table 9 below.

The data generated in this trial indicate that treatment of tomatoes with Messenger®, either through field sprays or as a post harvest dip, resulted in earlier fruit red ripening compared to grower's standard. In addition, although early ripening was observed, the Messenger® treatments maintained the red ripe condition longer than the grower's standard with delay of breakdown and decay.

Example 10

Effect on Messenger on Post Harvested Maturity and Fruit Decay of Tomato Under Cold Storage Conditions The tomatoes were grown under either standard conditions (identified in Example 8) or full Messenger® treatment over the course of the growing season (identified in Example 8) and then hand picked at the time of commercial harvest. Mature green fruit of uniform size (5/6) were collected throughout the field in four replicate samples of 25 fruit per sample, placed directly into fruit bags and transported to a laboratory facility for postharvest treatment and/or analysis. Four different treatment regimen were examined as follows:

(1) Fruits from Messenger® treated plots received no additional treatment following harvest;

(2) Fruits from Messenger® treated plots were further treated with Messenger® after harvest;

(3) Fruits from standard plots were treated with Messenger® after harvest; and (4) Fruits from standard plots received no additional treatment following harvest.

Postharvest treatment of fruits from groups (2) and (3) were carried out by dipping the fruit in a Messenger® solution (20 ppm harpin$_{Ea}$). The postharvest treated tomatoes were allowed to air dry and then tomatoes from groups (1)-(4) were marked and mixed together in tomato crates for storage in a Custom Packing House cooler at 11° C. (52° F.). The tomatoes were then rated for color development and decay over time using the rating scale described in Example 8. The results of this study appear in Table 10 below.

TABLE 9

Affect of Preharvest and Postharvest Treatment on Maturity and Decay

| Group | Days After Treatment | Grade 1 | 2 | 3 | 4 | 5 | Index | Efficacy | T-test p < 0.05 | p < 0.01 |
|---|---|---|---|---|---|---|---|---|---|---|
| 1 | 10 | 11 | 6 | 8 | 75 | 0 | 0.69 | 7.28% | yes | yes |
| 2 | 10 | 5 | 7 | 11 | 77 | 0 | 0.72 | 3.81% | yes | yes |
| 3 | 10 | 5 | 3 | 6 | 86 | 1 | 0.75 | N/A | N/A | N/A |
| 1 | 14 | 4 | 5 | 5 | 86 | 0 | 0.75 | 2.61% | yes | yes |
| 2 | 14 | 2 | 6 | 5 | 87 | 0 | 0.75 | 1.57% | yes | yes |
| 3 | 14 | 2 | 4 | 4 | 89 | 1 | 0.77 | N/A | N/A | N/A |
| 1 | 17 | 0 | 0 | 3 | 92 | 5 | 0.80 | 3.37% | yes | yes |
| 2 | 17 | 0 | 1 | 4 | 82 | 13 | 0.81 | 2.16% | yes | yes |
| 3 | 17 | 0 | 0 | 1 | 82 | 17 | 0.83 | N/A | N/A | N/A |
| 1 | 20 | 0 | 0 | 0 | 89 | 11 | 0.82 | 2.61% | yes | yes |
| 2 | 20 | 0 | 0 | 0 | 80 | 20 | 0.84 | 0.47% | yes | yes |
| 3 | 20 | 0 | 0 | 1 | 76 | 23 | 0.84 | N/A | N/A | N/A |

TABLE 10

Affect of Preharvest and Postharvest Treatment on Maturity and Decay

| Group | Days After Treatment | Grade 1 | 2 | 3 | 4 | 5 | Index | Efficacy | T-test p < 0.05 | p < 0.01 |
|---|---|---|---|---|---|---|---|---|---|---|
| 1 | 7 | 66 | 34 | 0 | 0 | 0 | 0.27 | 0.00% | yes | yes |
| 2 | 7 | 67 | 33 | 0 | 0 | 0 | 0.27 | 0.75% | yes | yes |
| 3 | 7 | 76 | 24 | 0 | 0 | 0 | 0.27 | 7.46% | yes | yes |
| 4 | 7 | 68 | 30 | 2 | 0 | 0 | 0.27 | N/A | yes | yes |
| 1 | 10 | 59 | 31 | 8 | 0 | 0 | 0.30 | 7.53% | yes | yes |
| 2 | 10 | 60 | 28 | 12 | 0 | 0 | 0.30 | 5.00% | yes | yes |
| 3 | 10 | 65 | 35 | 0 | 0 | 0 | 0.27 | 15.63% | yes | yes |
| 4 | 10 | 49 | 42 | 9 | 0 | 0 | 0.32 | N/A | N/A | N/A |
| 1 | 17 | 19 | 35 | 28 | 18 | 0 | 0.49 | 7.20% | yes | yes |
| 2 | 17 | 20 | 38 | 28 | 14 | 0 | 0.47 | 10.61% | yes | yes |
| 3 | 17 | 19 | 28 | 39 | 14 | 0 | 0.50 | 6.06% | yes | yes |
| 4 | 17 | 17 | 27 | 31 | 25 | 0 | 0.53 | N/A | N/A | N/A |
| 1 | 21 | 11 | 28 | 29 | 32 | 0 | 0.56 | 6.62% | N/A | N/A |
| 2 | 21 | 15 | 26 | 37 | 22 | 0 | 0.53 | 11.92% | yes | yes |
| 3 | 21 | 10 | 33 | 35 | 22 | 0 | 0.54 | 10.93% | yes | yes |
| 4 | 21 | 10 | 18 | 32 | 40 | 0 | 0.60 | N/A | N/A | N/A |
| 1 | 26 | 3 | 15 | 23 | 59 | 0 | 0.68 | −2.26% | yes | yes |
| 2 | 26 | 9 | 19 | 25 | 41 | 6 | 0.63 | 4.39% | yes | yes |
| 3 | 26 | 3 | 23 | 31 | 43 | 0 | 0.63 | 5.00% | yes | yes |
| 4 | 26 | 2 | 19 | 23 | 50 | 1 | 0.66 | N/A | N/A | N/A |
| 1 | 32 | 3 | 15 | 23 | 59 | 0 | 0.68 | −2.26% | yes | yes |
| 2 | 32 | 9 | 19 | 25 | 41 | 6 | 0.63 | 4.39% | yes | yes |
| 3 | 32 | 3 | 23 | 31 | 43 | 0 | 0.63 | 5.00% | yes | yes |
| 4 | 32 | 2 | 19 | 23 | 50 | 1 | 0.66 | N/A | N/A | N/A |
| 1 | 38 | 0 | 4 | 10 | 84 | 2 | 0.77 | 0.26% | yes | yes |
| 2 | 38 | 1 | 10 | 15 | 65 | 9 | 0.74 | 3.64% | yes | yes |
| 3 | 38 | 1 | 5 | 14 | 78 | 2 | 0.75 | 2.60% | yes | yes |
| 4 | 38 | 0 | 3 | 13 | 80 | 4 | 0.77 | N/A | N/A | N/A |
| 1 | 45 | 0 | 3 | 11 | 74 | 12 | 0.79 | 2.95% | yes | yes |
| 2 | 45 | 1 | 4 | 12 | 69 | 14 | 0.78 | 3.93% | yes | yes |
| 3 | 45 | 0 | 1 | 11 | 81 | 7 | 0.79 | 3.19% | yes | yes |
| 4 | 45 | 0 | 0 | 10 | 73 | 17 | 0.81 | N/A | N/A | N/A |
| 1 | 50 | 0 | 3 | 10 | 63 | 23 | 0.82 | 3.55% | yes | yes |
| 2 | 50 | 0 | 4 | 11 | 58 | 27 | 0.82 | 3.55% | yes | yes |
| 3 | 50 | 0 | 0 | 8 | 78 | 14 | 0.81 | 4.02% | yes | yes |
| 4 | 50 | 0 | 0 | 3 | 71 | 26 | 0.85 | N/A | N/A | N/A |
| 1 | 55 | 0 | 0 | 0 | 73 | 27 | 0.85 | 1.84% | yes | yes |
| 2 | 55 | 0 | 0 | 0 | 68 | 32 | 0.86 | 0.69% | yes | yes |
| 3 | 55 | 0 | 0 | 2 | 80 | 18 | 0.83 | 4.37% | yes | yes |
| 4 | 55 | 0 | 0 | 0 | 65 | 35 | 0.87 | N/A | N/A | N/A |
| 1 | 60 | 0 | 0 | 0 | 65 | 35 | 0.87 | 2.47% | yes | yes |
| 2 | 60 | 0 | 0 | 0 | 63 | 37 | 0.87 | 2.02% | yes | yes |
| 3 | 60 | 0 | 0 | 0 | 74 | 26 | 0.85 | 4.48% | yes | yes |
| 4 | 60 | 0 | 0 | 0 | 54 | 46 | 0.89 | N/A | N/A | N/A |
| 1 | 65 | 0 | 0 | 0 | 53 | 47 | 0.89 | 1.76% | yes | yes |
| 2 | 65 | 0 | 0 | 0 | 58 | 42 | 0.88 | 2.86% | yes | yes |
| 3 | 65 | 0 | 0 | 0 | 65 | 35 | 0.87 | 4.40% | yes | yes |
| 4 | 65 | 0 | 0 | 0 | 45 | 55 | 0.91 | N/A | N/A | N/A |

In previous trials when tomatoes were treated with Messenger® in the field and/or with a post harvest dip, the fruit appeared to develop to red ripe more quickly than the grower's standard, when held at ambient temperatures (75-80° F.). Although this early ripening was observed, these red fruit did not begin to decay earlier than the grower's standard. In this study, the fruit were held at a constant 52° F. in a commercial cold storage room at a tomato packinghouse facility. It appears that this lower temperature slows the ripening process, as would be expected, and Messenger® treatments did not increase the rate of the red ripening for the first 30 days, as observed in previous tests. The Messenger® treatments did, however, seem to maintain the red ripe condition longer than the grower's standard without breakdown and decay.

Example 11

Effect of Messenger on Post Harvested Maturity and Fruit Decay on Tomato

The tomatoes were grown under either standard conditions (identified in Example 8) or full Messenger® treatment over the course of the growing season (identified in Example 8) and then hand picked at the time of commercial harvest. Mature green fruit of uniform size (5/6) were collected throughout the field in four replicate samples of 25 fruit per sample, placed directly into fruit bags and transported to a laboratory facility for postharvest treatment and/or analysis. Four different treatment regimen were examined as follows:
(1) Fruits from Messenger® treated plots received no additional treatment following harvest;
(2) Fruits from Messenger® treated plots were further treated with Messenger® after harvest;
(3) Fruits from standard plots were treated with Messenger® after harvest; and
(4) Fruits from standard plots received no additional treatment following harvest.

Postharvest treatment of fruits from groups (2) and (3) were carried out by dipping the fruit in a Messenger® solution (20 ppm harpin$_{Ea}$). The postharvest treated tomatoes were allowed to air dry and then tomatoes from groups (1)-(4) were marked and mixed together in tomato crates for storage. Storage temperatures ranged from about 23 to 26° C. (75-80° F.). The tomatoes were then rated for color development and decay over time using the commercial rating scale from the Florida Tomato Committee color guide as follows:

| Grade | Description |
|---|---|
| 1 | Green: When fruit cut in half, no seeds cut; fruit entirely green with no color break; |
| 2 | Breakers: Initial sign of color break on 10% or less of the area of fruit; these areas are usually pink; |
| 3 | Turning: Pink or red on 10 to 30% of the fruit surface; |
| 4 | Pink: Pink or red on 30 to 60% of the fruit surface; |
| 5 | Light Red: Pink on over 60% of fruit surface and red color no more than 90% of fruit surface; |
| 6 | Red: Fruit totally red in color; and |
| 7 | Decay: Some areas of the fruit beginning to break down from decay. |

The results of this treatment are set forth in Table 11 below.

TABLE 11

Affect of Preharvest and Postharvest Treatment on Maturity and Decay Data

| Group | Days After Treatment | Grade | | | | | | | Index | Efficacy | T-test p < 0.05 | p < 0.01 |
|---|---|---|---|---|---|---|---|---|---|---|---|---|
| | | 1 | 2 | 3 | 4 | 5 | 6 | 7 | | | | |
| 1 | 3 | 80 | 18 | 2 | 0 | 0 | 0 | 0 | 0.17 | 0.00% | no | no |
| 2 | 3 | 73 | 17 | 9 | 1 | 0 | 0 | 0 | 0.20 | −13.11% | yes | yes |
| 3 | 3 | 78 | 19 | 3 | 0 | 0 | 0 | 0 | 0.18 | −2.46% | yes | yes |
| 4 | 3 | 80 | 18 | 2 | 0 | 0 | 0 | 0 | 0.17 | N/A | no | no |
| 1 | 7 | 36 | 23 | 22 | 12 | 5 | 2 | 0 | 0.33 | 3.72% | yes | no |
| 2 | 7 | 37 | 23 | 17 | 19 | 4 | 0 | 0 | 0.33 | 4.96% | yes | no |
| 3 | 7 | 40 | 17 | 15 | 18 | 9 | 1 | 0 | 0.35 | 0.00% | yes | no |
| 4 | 7 | 35 | 22 | 19 | 15 | 8 | 1 | 0 | 0.35 | N/A | no | no |
| 1 | 14 | 2 | 5 | 8 | 8 | 13 | 65 | 0 | 0.74 | 8.02% | yes | yes |
| 2 | 14 | 2 | 3 | 5 | 9 | 8 | 72 | 1 | 0.77 | 4.44% | yes | yes |
| 3 | 14 | 4 | 4 | 7 | 8 | 17 | 60 | 0 | 0.73 | 9.41% | yes | yes |
| 4 | 14 | 0 | 0 | 6 | 5 | 13 | 72 | 4 | 0.80 | N/A | no | no |
| 1 | 17 | 0 | 0 | 2 | 3 | 6 | 89 | 0 | 0.83 | 2.51% | yes | yes |
| 2 | 17 | 1 | 1 | 1 | 0 | 7 | 88 | 2 | 0.83 | 2.35% | yes | yes |
| 3 | 17 | 1 | 2 | 0 | 0 | 9 | 88 | 0 | 0.83 | 3.18% | yes | yes |
| 4 | 17 | 0 | 0 | 0 | 0 | 7 | 89 | 4 | 0.85 | N/A | no | no |
| 1 | 21 | 0 | 0 | 0 | 0 | 0 | 97 | 3 | 0.86 | 1.31% | yes | yes |
| 2 | 21 | 0 | 0 | 0 | 0 | 0 | 97 | 3 | 10.86 | 1.31% | yes | yes |
| 3 | 21 | 0 | 0 | 0 | 0 | 3 | 95 | 2 | 0.86 | 1.96% | yes | yes |
| 4 | 21 | 0 | 0 | 0 | 0 | 1 | 87 | 12 | 0.87 | N/A | no | no |
| 1 | 28 | 0 | 0 | 0 | 0 | 0 | 85 | 15 | 0.88 | 2.84% | yes | yes |
| 2 | 28 | 0 | 0 | 0 | 0 | 0 | 91 | 9 | 0.87 | 3.79% | yes | yes |
| 3 | 28 | 0 | 0 | 0 | 0 | 0 | 81 | 19 | 0.88 | 2.21% | yes | yes |
| 4 | 28 | 0 | 0 | 0 | 0 | 0 | 67 | 33 | 0.90 | N/A | no | no |
| 1 | 32 | 0 | 0 | 0 | 0 | 0 | 22 | 78 | 0.97 | 2.16% | yes | yes |
| 2 | 32 | 0 | 0 | 0 | 0 | 0 | 16 | 84 | 0.98 | 1.30% | yes | yes |
| 3 | 32 | 0 | 0 | 0 | 0 | 0 | 55 | 45 | 0.92 | 6.93% | yes | yes |
| 4 | 32 | 0 | 0 | 0 | 0 | 0 | 7 | 93 | 0.99 | N/A | no | no |
| 1 | 37 | 0 | 0 | 0 | 0 | 0 | 14 | 86 | 0.98 | 1.15% | yes | yes |
| 2 | 37 | 0 | 0 | 0 | 0 | 0 | 7 | 93 | 0.00 | 0.14% | yes | yes |
| 3 | 37 | 0 | 0 | 0 | 0 | 0 | 9 | 91 | 0.99 | 0.43% | yes | yes |
| 4 | 37 | 0 | 0 | 0 | 0 | 0 | 6 | 94 | 0.99 | N/A | no | no |
| 1 | 42 | 0 | 0 | 0 | 0 | 0 | 12 | 88 | 0.98 | 1.01% | yes | yes |
| 2 | 42 | 0 | 0 | 0 | 0 | 0 | 7 | 93 | 0.99 | 0.29% | yes | yes |
| 3 | 42 | 0 | 0 | 0 | 0 | 0 | 8 | 92 | 0.99 | 0.43% | yes | yes |
| 4 | 42 | 0 | 0 | 0 | 0 | 0 | 5 | 95 | 0.99 | N/A | no | no |
| 1 | 45 | 0 | 0 | 0 | 0 | 0 | 8 | 92 | 0.99 | 0.57% | no | no |
| 2 | 45 | 0 | 0 | 0 | 0 | 0 | 4 | 96 | 0.99 | 0.00% | no | no |
| 3 | 45 | 0 | 0 | 0 | 0 | 0 | 4 | 96 | 0.99 | 0.00% | no | no |
| 4 | 45 | 0 | 0 | 0 | 0 | 0 | 4 | 96 | 0.99 | N/A | no | no |
| 1 | 50 | 0 | 0 | 0 | 0 | 0 | 7 | 93 | 0.99 | 0.43% | no | no |
| 2 | 50 | 0 | 0 | 0 | 0 | 0 | 4 | 96 | 0.99 | 0.00% | no | no |
| 3 | 50 | 0 | 0 | 0 | 0 | 0 | 4 | 96 | 0.99 | 0.00% | no | no |
| 4 | 50 | 0 | 0 | 0 | 0 | 0 | 4 | 96 | 0.99 | N/A | no | no |

In previous trials tomatoes treated with Messenger® in the field and/or with a post harvest dip appeared to develop to red ripe more quickly, but decayed slower than the grower's standard. The data generated from this trial support these observations. By twenty-one days post harvest, 97% of the Messenger® treated tomatoes were full red ripe, compared to 87% of the grower's standard. Although it may be assumed that fruit which reach maturity more quickly will also start to break down more quickly, the results of the present Examples surprisingly demonstrate that these earlier-maturing tomatoes were actually 15% slower to decay than the grower's standard tomatoes. This phenomenon should be of great interest of several segments of the tomato market. The growers may be able to reduce ethylene gashouse timings, and the retail market should be able to significantly reduce inventory shrinkage.

Although the invention has been described in detail for the purpose of illustration, it is understood that such detail is solely for that purpose, and variations can be made therein by those skilled in the art without departing from the spirit and scope of the invention which is defined by the following claims.

```
                        SEQUENCE LISTING

<160> NUMBER OF SEQ ID NOS: 12

<210> SEQ ID NO 1
<211> LENGTH: 338
<212> TYPE: PRT
<213> ORGANISM: Erwinia chrysanthemi

<400> SEQUENCE: 1

Met Gln Ile Thr Ile Lys Ala His Ile Gly Gly Asp Leu Gly Val Ser
 1               5                  10                  15

Gly Leu Gly Ala Gln Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
    50                  55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
        115                 120                 125

Leu Ala Asn Ser Met Leu Asn Ala Ser Gln Met Thr Gln Gly Asn Met
    130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
            180                 185                 190

Gly Asn Ala Ile Gly Met Gly Val Gly Gln Asn Ala Ala Leu Ser Ala
        195                 200                 205

Leu Ser Asn Val Ser Thr His Val Asp Gly Asn Asn Arg His Phe Val
    210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
            260                 265                 270

Pro Asp Asp Asp Gly Met Thr Gly Ala Ser Met Asp Lys Phe Arg Gln
        275                 280                 285
```

```
Ala Met Gly Met Ile Lys Ser Ala Val Ala Gly Asp Thr Gly Asn Thr
    290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala

<210> SEQ ID NO 2
<211> LENGTH: 2141
<212> TYPE: DNA
<213> ORGANISM: Erwinia chrysanthemi

<400> SEQUENCE: 2
cgattttacc cgggtgaacg tgctatgacc gacagcatca cggtattcga caccgttacg      60
gcgtttatgg ccgcgatgaa ccggcatcag cggcgcgct ggtcgccgca atccggcgtc     120
gatctggtat ttcagtttgg ggacaccggg cgtgaactca tgatgcagat tcagccgggg     180
cagcaatatc ccggcatgtt gcgcacgctg ctcgctcgtc gttatcagca ggcggcagag     240
tgcgatggct gccatctgtg cctgaacggc agcgatgtat tgatcctctg gtggccgctg     300
ccgtcggatc ccggcagtta ccgcaggtg atcgaacgtt tgtttgaact ggcgggaatg     360
acgttgccgt cgctatccat agcaccgacg gcgcgtccgc agacagggaa cggacgcgcc     420
cgatcattaa gataaaggcg gcttttttta ttgcaaaacg gtaacggtga ggaaccgttt     480
caccgtcggc gtcactcagt aacaagtatc catcatgatg cctacatcgg gatcggcgtg     540
ggcatccgtt gcagatactt tgcgaacac ctgacatgaa tgaggaaacg aaattatgca     600
aattacgatc aaagcgcaca tcggcggtga tttgggcgtc tccggtctgg ggctgggtgc     660
tcagggactg aaaggactga attccgcggc ttcatcgctg ggttccagcg tggataaact     720
gagcagcacc atcgataagt tgacctccgc gctgacttcg atgatgtttg cggcgcgct     780
ggcgcagggg ctgggcgcca gctcgaaggg gctgggatg agcaatcaac tgggccagtc     840
tttcggcaat ggcgcgcagg gtgcgagcaa cctgctatcc gtaccgaaat ccggcggcga     900
tgcgttgtca aaatgtttg ataaagcgct ggacgatctg ctgggtcatg acaccgtgac     960
caagctgact aaccagagca accaactggc taattcaatg ctgaacgcca gccagatgac    1020
ccagggtaat atgaatgcgt tcggcagcgg tgtgaacaac gcactgtcgt ccattctcgg    1080
caacggtctc ggccagtcga tgagtggctt ctctcagcct tctctggggg caggcggctt    1140
gcagggcctg agcggcgcgg gtgcattcaa ccagttgggt aatgccatcg gcatgggcgt    1200
ggggcagaat gctgcgctga gtgcgttgag taacgtcagc acccacgtag acggtaacaa    1260
ccgccacttt gtagataaag aagatcgcgg catggcgaaa gagatcggcc agtttatgga    1320
tcagtatccg gaaatattcg gtaaaccgga ataccagaaa gatggctgga gttcgccgaa    1380
gacggacgac aaatcctggg ctaaagcgct gagtaaaccg gatgatgacg gtatgaccgg    1440
cgccagcatg gacaaattcc gtcaggcgat gggtatgatc aaaagcgcgg tggcgggtga    1500
taccggcaat accaacctga acctgcgtgg cgcgggcggt gcatcgctgg gtatcgatgc    1560
ggctgtcgtc ggcgataaaa tagccaacat gtcgctgggg aagctggcca acgcctgata    1620
atctgtgctg gcctgataaa gcggaaacga aaaagagac ggggaagcct gtctcttttc    1680
ttattatgcg gttatgcgg ttacctggac cggttaatca tcgtcatcga tctggtacaa    1740
acgcacattt tcccgttcat tcgcgtcgtt acgcgccaca atcgcgatgg catcttcctc    1800
```

-continued

```
gtcgctcaga ttgcgcggct gatggggaac gccgggtgga atatagagaa actcgccggc    1860
cagatggaga cacgtctgcg ataaatctgt gccgtaacgt gtttctatcc gcccctttag    1920
cagatagatt gcggtttcgt aatcaacatg gtaatgcggt tccgcctgtg cgccggccgg    1980
gatcaccaca atattcatag aaagctgtct tgcacctacc gtatcgcggg agataccgac    2040
aaaatagggc agttttgcg tggtatccgt ggggtgttcc ggcctgacaa tcttgagttg     2100
gttcgtcatc atctttctcc atctgggcga cctgatcggt t                        2141
```

<210> SEQ ID NO 3
<211> LENGTH: 403
<212> TYPE: PRT
<213> ORGANISM: Erwinia amylovora

<400> SEQUENCE: 3

Met Ser Leu Asn Thr Ser Gly Leu Gly Ala Ser Thr Met Gln Ile Ser
1 5 10 15

Ile Gly Gly Ala Gly Gly Asn Asn Gly Leu Leu Gly Thr Ser Arg Gln
20 25 30

Asn Ala Gly Leu Gly Gly Asn Ser Ala Leu Gly Leu Gly Gly Gly Asn
35 40 45

Gln Asn Asp Thr Val Asn Gln Leu Ala Gly Leu Leu Thr Gly Met Met
50 55 60

Met Met Met Ser Met Met Gly Gly Gly Gly Leu Met Gly Gly Gly Leu
65 70 75 80

Gly Gly Gly Leu Gly Asn Gly Leu Gly Gly Ser Gly Gly Leu Gly Glu
85 90 95

Gly Leu Ser Asn Ala Leu Asn Asp Met Leu Gly Gly Ser Leu Asn Thr
100 105 110

Leu Gly Ser Lys Gly Gly Asn Asn Thr Thr Ser Thr Thr Asn Ser Pro
115 120 125

Leu Asp Gln Ala Leu Gly Ile Asn Ser Thr Ser Gln Asn Asp Asp Ser
130 135 140

Thr Ser Gly Thr Asp Ser Thr Ser Asp Ser Ser Asp Pro Met Gln Gln
145 150 155 160

Leu Leu Lys Met Phe Ser Glu Ile Met Gln Ser Leu Phe Gly Asp Gly
165 170 175

Gln Asp Gly Thr Gln Gly Ser Ser Ser Gly Gly Lys Gln Pro Thr Glu
180 185 190

Gly Glu Gln Asn Ala Tyr Lys Lys Gly Val Thr Asp Ala Leu Ser Gly
195 200 205

Leu Met Gly Asn Gly Leu Ser Gln Leu Leu Gly Asn Gly Gly Leu Gly
210 215 220

Gly Gly Gln Gly Gly Asn Ala Gly Thr Gly Leu Asp Gly Ser Ser Leu
225 230 235 240

Gly Gly Lys Gly Leu Gln Asn Leu Ser Gly Pro Val Asp Tyr Gln Gln
245 250 255

Leu Gly Asn Ala Val Gly Thr Gly Ile Gly Met Lys Ala Gly Ile Gln
260 265 270

Ala Leu Asn Asp Ile Gly Thr His Arg His Ser Ser Thr Arg Ser Phe
275 280 285

Val Asn Lys Gly Asp Arg Ala Met Ala Lys Glu Ile Gly Gln Phe Met
290 295 300

Asp Gln Tyr Pro Glu Val Phe Gly Lys Pro Gln Tyr Gln Lys Gly Pro
305 310 315 320

```
Gly Gln Glu Val Lys Thr Asp Asp Lys Ser Trp Ala Lys Ala Leu Ser
                325                 330                 335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
        355                 360                 365

Gly Asn Leu Gln Ala Arg Gly Ala Gly Gly Ser Ser Leu Gly Ile Asp
    370                 375                 380

Ala Met Met Ala Gly Asp Ala Ile Asn Asn Met Ala Leu Gly Lys Leu
385                 390                 395                 400

Gly Ala Ala

<210> SEQ ID NO 4
<211> LENGTH: 1288
<212> TYPE: DNA
<213> ORGANISM: Erwinia amylovora

<400> SEQUENCE: 4
aagcttcggc atggcacgtt tgaccgttgg gtcggcaggg tacgtttgaa ttattcataa      60
gaggaatacg ttatgagtct gaatacaagt gggctgggag cgtcaacgat gcaaatttct     120
atcggcggtg cgggcggaaa taacgggttg ctgggtacca gtcgccagaa tgctgggttg     180
ggtggcaatt ctgcactggg gctgggcggc ggtaatcaaa atgataccgt caatcagctg     240
gctggcttac tcaccggcat gatgatgatg atgagcatga tgggcggtgg tgggctgatg     300
ggcggtggct taggcggtgg cttaggtaat ggcttgggtg gctcaggtgg cctgggcgaa     360
ggactgtcga acgcgctgaa cgatatgtta ggcggttcgc tgaacacgct gggctcgaaa     420
ggcggcaaca ataccacttc aacaacaaat tccccgctgg accaggcgct gggtattaac     480
tcaacgtccc aaaacgacga ttccacctcc ggcacagatt ccacctcaga ctccagcgac     540
ccgatgcagc agctgctgaa gatgttcagc gagataatgc aaagcctgtt tggtgatggg     600
caagatggca cccagggcag ttcctctggg ggcaagcagc cgaccgaagg cgagcagaac     660
gcctataaaa aaggagtcac tgatgcgctg tcgggcctga tgggtaatgg tctgagccag     720
ctccttggca acgggggact gggaggtggt cagggcggta atgctggcac gggtcttgac     780
ggttcgtcgc tggcggcaa agggctgcaa aacctgagcg gccggtgga ctaccagcag     840
ttaggtaacg ccgtgggtac cggtatcggt atgaaagcgg gcattcaggc gctgaatgat     900
atcggtacgc acaggcacag ttcaacccgt tctttcgtca ataaaggcga tcgggcgatg     960
gcgaaggaaa tcggtcagtt catggaccag tatcctgagg tgtttggcaa gccgcagtac    1020
cagaaaggcc cgggtcagga ggtgaaaacc gatgacaaat catgggcaaa agcactgagc    1080
aagccagatg acgacggaat gacaccagcc agtatggagc agttcaacaa agccaagggc    1140
atgatcaaaa ggcccatggc gggtgatacc ggcaacggca acctgcaggc acgcggtgcc    1200
ggtggttctt cgctgggtat tgatgccatg atggccggtg atgccattaa caatatggca    1260
cttggcaagc tgggcgcggc ttaagctt                                       1288

<210> SEQ ID NO 5
<211> LENGTH: 447
<212> TYPE: PRT
<213> ORGANISM: Erwinia amylovora

<400> SEQUENCE: 5

Met Ser Ile Leu Thr Leu Asn Asn Asn Thr Ser Ser Ser Pro Gly Leu
1               5                   10                  15
```

```
Phe Gln Ser Gly Gly Asp Asn Gly Leu Gly Gly His Asn Ala Asn Ser
             20                  25                  30

Ala Leu Gly Gln Gln Pro Ile Asp Arg Gln Thr Ile Glu Gln Met Ala
         35                  40                  45

Gln Leu Leu Ala Glu Leu Leu Lys Ser Leu Leu Ser Pro Gln Ser Gly
     50                  55                  60

Asn Ala Ala Thr Gly Ala Gly Asn Asp Gln Thr Thr Gly Val Gly
 65                  70                  75                  80

Asn Ala Gly Gly Leu Asn Gly Arg Lys Gly Thr Ala Gly Thr Thr Pro
                 85                  90                  95

Gln Ser Asp Ser Gln Asn Met Leu Ser Glu Met Gly Asn Asn Gly Leu
             100                 105                 110

Asp Gln Ala Ile Thr Pro Asp Gly Gln Gly Gly Gly Gln Ile Gly Asp
         115                 120                 125

Asn Pro Leu Leu Lys Ala Met Leu Lys Leu Ile Ala Arg Met Met Asp
     130                 135                 140

Gly Gln Ser Asp Gln Phe Gly Gln Pro Gly Thr Gly Asn Asn Ser Ala
145                 150                 155                 160

Ser Ser Gly Thr Ser Ser Ser Gly Gly Ser Pro Phe Asn Asp Leu Ser
                 165                 170                 175

Gly Gly Lys Ala Pro Ser Gly Asn Ser Pro Ser Gly Asn Tyr Ser Pro
             180                 185                 190

Val Ser Thr Phe Ser Pro Pro Ser Thr Pro Thr Ser Pro Thr Ser Pro
         195                 200                 205

Leu Asp Phe Pro Ser Ser Pro Thr Lys Ala Ala Gly Gly Ser Thr Pro
 210                 215                 220

Val Thr Asp His Pro Asp Pro Val Gly Ser Ala Gly Ile Gly Ala Gly
225                 230                 235                 240

Asn Ser Val Ala Phe Thr Ser Ala Gly Ala Asn Gln Thr Val Leu His
                 245                 250                 255

Asp Thr Ile Thr Val Lys Ala Gly Gln Val Phe Asp Gly Lys Gly Gln
             260                 265                 270

Thr Phe Thr Ala Gly Ser Glu Leu Gly Asp Gly Gln Ser Glu Asn
         275                 280                 285

Gln Lys Pro Leu Phe Ile Leu Glu Asp Gly Ala Ser Leu Lys Asn Val
     290                 295                 300

Thr Met Gly Asp Asp Gly Ala Asp Gly Ile His Leu Tyr Gly Asp Ala
305                 310                 315                 320

Lys Ile Asp Asn Leu His Val Thr Asn Val Gly Glu Asp Ala Ile Thr
                 325                 330                 335

Val Lys Pro Asn Ser Ala Gly Lys Lys Ser His Val Glu Ile Thr Asn
             340                 345                 350

Ser Ser Phe Glu His Ala Ser Asp Lys Ile Leu Gln Leu Asn Ala Asp
         355                 360                 365

Thr Asn Leu Ser Val Asp Asn Val Lys Ala Lys Asp Phe Gly Thr Phe
     370                 375                 380

Val Arg Thr Asn Gly Gly Gln Gln Gly Asn Trp Asp Leu Asn Leu Ser
385                 390                 395                 400

His Ile Ser Ala Glu Asp Gly Lys Phe Ser Phe Val Lys Ser Asp Ser
                 405                 410                 415

Glu Gly Leu Asn Val Asn Thr Ser Asp Ile Ser Leu Gly Asp Val Glu
             420                 425                 430

Asn His Tyr Lys Val Pro Met Ser Ala Asn Leu Lys Val Ala Glu
         435                 440                 445
```

<210> SEQ ID NO 6
<211> LENGTH: 1344
<212> TYPE: DNA
<213> ORGANISM: Erwinia amylovora

<400> SEQUENCE: 6

```
atgtcaattc ttacgcttaa caacaatacc tcgtcctcgc cgggtctgtt ccagtccggg     60
ggggacaacg ggcttggtgg tcataatgca aattctgcgt tggggcaaca acccatcgat    120
cggcaaacca ttgagcaaat ggctcaatta ttggcggaac tgttaaagtc actgctatcg    180
ccacaatcag gtaatgcggc aaccggagcc ggtggcaatg accagactac aggagttggt    240
aacgctggcg gcctgaacgg acgaaaaggc acagcaggaa ccactccgca gtctgacagt    300
cagaacatgc tgagtgagat gggcaacaac gggctggatc aggccatcac gcccgatggc    360
cagggcggcg ggcagatcgg cgataatcct ttactgaaag ccatgctgaa gcttattgca    420
cgcatgatgg acggccaaag cgatcagttt ggccaacctg gtacgggcaa caacagtgcc    480
tcttccggta cttcttcatc tggcggttcc ccttttaacg atctatcagg ggggaaggcc    540
ccttccggca actccccttc cggcaactac tctcccgtca gtaccttctc acccccatcc    600
acgccaacgt cccctacctc accgcttgat ttcccttctt ctcccaccaa agcagccggg    660
ggcagcacgc cggtaaccga tcatcctgac cctgttggta gcgcgggcat cggggccgga    720
aattcggtgg ccttcaccag cgccggcgct aatcagacgg tgctgcatga caccattacc    780
gtgaaagcgg gtcaggtgtt tgatggcaaa ggacaaacct tcaccgccgg ttcagaatta    840
ggcgatggcg gccagtctga aaccagaaa ccgctgttta tactggaaga cggtgccagc     900
ctgaaaaacg tcaccatggg cgacgacggg gcggatggta ttcatcttta cggtgatgcc    960
aaaatagaca atctgcacgt caccaacgtg ggtgaggacg cgattaccgt taagccaaac   1020
agcgcgggca aaaaatccca cgttgaaatc actaacagtt ccttcgagca cgcctctgac   1080
aagatcctgc agctgaatgc cgatactaac ctgagcgttg acaacgtgaa ggccaaagac   1140
tttggtactt ttgtacgcac taacggcggt caacagggta actgggatct gaatctgagc   1200
catatcagcg cagaagacgg taagttctcg ttcgttaaaa gcgatagcga ggggctaaac   1260
gtcaatacca gtgatatctc actgggtgat gttgaaaacc actacaaagt gccgatgtcc   1320
gccaacctga aggtggctga atga                                          1344
```

<210> SEQ ID NO 7
<211> LENGTH: 341
<212> TYPE: PRT
<213> ORGANISM: Pseudomonas syringae

<400> SEQUENCE: 7

```
Met Gln Ser Leu Ser Leu Asn Ser Ser Ser Leu Gln Thr Pro Ala Met
  1               5                  10                  15

Ala Leu Val Leu Val Arg Pro Glu Ala Glu Thr Thr Gly Ser Thr Ser
             20                  25                  30

Ser Lys Ala Leu Gln Glu Val Val Val Lys Leu Ala Glu Glu Leu Met
         35                  40                  45

Arg Asn Gly Gln Leu Asp Asp Ser Ser Pro Leu Gly Lys Leu Leu Ala
     50                  55                  60

Lys Ser Met Ala Ala Asp Gly Lys Ala Gly Gly Gly Ile Glu Asp Val
 65                  70                  75                  80

Ile Ala Ala Leu Asp Lys Leu Ile His Glu Lys Leu Gly Asp Asn Phe
                 85                  90                  95
```

```
Gly Ala Ser Ala Asp Ser Ala Ser Gly Thr Gly Gln Gln Asp Leu Met
                100                 105                 110
Thr Gln Val Leu Asn Gly Leu Ala Lys Ser Met Leu Asp Asp Leu Leu
            115                 120                 125
Thr Lys Gln Asp Gly Gly Thr Ser Phe Ser Glu Asp Asp Met Pro Met
        130                 135                 140
Leu Asn Lys Ile Ala Gln Phe Met Asp Asp Asn Pro Ala Gln Phe Pro
145                 150                 155                 160
Lys Pro Asp Ser Gly Ser Trp Val Asn Glu Leu Lys Glu Asp Asn Phe
                165                 170                 175
Leu Asp Gly Asp Glu Thr Ala Ala Phe Arg Ser Ala Leu Asp Ile Ile
            180                 185                 190
Gly Gln Gln Leu Gly Asn Gln Gln Ser Asp Ala Gly Ser Leu Ala Gly
        195                 200                 205
Thr Gly Gly Gly Leu Gly Thr Pro Ser Ser Phe Ser Asn Asn Ser Ser
    210                 215                 220
Val Met Gly Asp Pro Leu Ile Asp Ala Asn Thr Gly Pro Gly Asp Ser
225                 230                 235                 240
Gly Asn Thr Arg Gly Glu Ala Gly Gln Leu Ile Gly Glu Leu Ile Asp
                245                 250                 255
Arg Gly Leu Gln Ser Val Leu Ala Gly Gly Leu Gly Thr Pro Val
            260                 265                 270
Asn Thr Pro Gln Thr Gly Thr Ser Ala Asn Gly Gly Gln Ser Ala Gln
        275                 280                 285
Asp Leu Asp Gln Leu Leu Gly Gly Leu Leu Leu Lys Gly Leu Glu Ala
    290                 295                 300
Thr Leu Lys Asp Ala Gly Gln Thr Gly Thr Asp Val Gln Ser Ser Ala
305                 310                 315                 320
Ala Gln Ile Ala Thr Leu Leu Val Ser Thr Leu Leu Gln Gly Thr Arg
                325                 330                 335
Asn Gln Ala Ala Ala
            340

<210> SEQ ID NO 8
<211> LENGTH: 1026
<212> TYPE: DNA
<213> ORGANISM: Pseudomonas syringae

<400> SEQUENCE: 8
atgcagagtc tcagtcttaa cagcagctcg ctgcaaaccc cggcaatggc ccttgtcctg    60
gtacgtcctg aagccgagac gactggcagt acgtcgagca aggcgcttca ggaagttgtc   120
gtgaagctgg ccgaggaact gatgcgcaat ggtcaactcg acgacagctc gccattggga   180
aaactgttgg ccaagtcgat ggccgcagat ggcaaggcgg cggcggtat tgaggatgtc    240 atcgctgcgc tggacaagct gatccatgaa agctcggtg acaacttcgg cgcgtctgcg    300
gacagcgcct cgggtaccgg acagcaggac ctgatgactc aggtgctcaa tggcctggcc   360
aagtcgatgc tcgatgatct tctgaccaag caggatggcg gacaagctt ctccgaagac    420 gatatgccga tgctgaacaa gatcgcgcag ttcatggatg acaatcccgc acagtttccc   480
aagccggact cgggctcctg ggtgaacgaa ctcaaggaag acaacttcct tgatggcgac   540
gaaacggctg cgttccgttc ggcactcgac atcattggcc agcaactggg taatcagcag   600
agtgacgctg gcagtctggc agggacgggt ggaggtctgg gcactccgag cagttttcc    660 aacaactcgt ccgtgatggg tgatccgctg atcgacgcca ataccggtcc cggtgacagc   720
```

```
ggcaataccc gtggtgaagc ggggcaactg atcggcgagc ttatcgaccg tggcctgcaa    780
tcggtattgg ccggtggtgg actgggcaca cccgtaaaca ccccgcagac cggtacgtcg    840
gcgaatggcg gacagtccgc tcaggatctt gatcagttgc tgggcggctt gctgctcaag    900
ggcctggagg caacgctcaa ggatgccggg caaacaggca ccgacgtgca gtcgagcgct    960
gcgcaaatcg ccaccttgct ggtcagtacg ctgctgcaag cacccgcaa tcaggctgca    1020 gcctga                                                              1026
```

<210> SEQ ID NO 9
<211> LENGTH: 424
<212> TYPE: PRT
<213> ORGANISM: Pseudomonas syringae

<400> SEQUENCE: 9

```
Met Ser Ile Gly Ile Thr Pro Arg Pro Gln Thr Thr Thr Pro Leu
  1               5                  10                  15

Asp Phe Ser Ala Leu Ser Gly Lys Ser Pro Gln Pro Asn Thr Phe Gly
                 20                  25                  30

Glu Gln Asn Thr Gln Gln Ala Ile Asp Pro Ser Ala Leu Leu Phe Gly
             35                  40                  45

Ser Asp Thr Gln Lys Asp Val Asn Phe Gly Thr Pro Asp Ser Thr Val
         50                  55                  60

Gln Asn Pro Gln Asp Ala Ser Lys Pro Asn Asp Ser Gln Ser Asn Ile
 65                  70                  75                  80

Ala Lys Leu Ile Ser Ala Leu Ile Met Ser Leu Leu Gln Met Leu Thr
                 85                  90                  95

Asn Ser Asn Lys Lys Gln Asp Thr Asn Gln Glu Gln Pro Asp Ser Gln
            100                 105                 110

Ala Pro Phe Gln Asn Asn Gly Gly Leu Gly Thr Pro Ser Ala Asp Ser
        115                 120                 125

Gly Gly Gly Gly Thr Pro Asp Ala Thr Gly Gly Gly Gly Asp Thr
    130                 135                 140

Pro Ser Ala Thr Gly Gly Gly Gly Asp Thr Pro Thr Ala Thr Gly
145                 150                 155                 160

Gly Gly Gly Ser Gly Gly Gly Gly Thr Pro Thr Ala Thr Gly Gly
                165                 170                 175

Ser Gly Gly Thr Pro Thr Ala Thr Gly Gly Gly Glu Gly Val Thr
            180                 185                 190

Pro Gln Ile Thr Pro Gln Leu Ala Asn Pro Asn Arg Thr Ser Gly Thr
        195                 200                 205

Gly Ser Val Ser Asp Thr Ala Gly Ser Thr Glu Gln Ala Gly Lys Ile
    210                 215                 220

Asn Val Val Lys Asp Thr Ile Lys Val Gly Ala Gly Glu Val Phe Asp
225                 230                 235                 240

Gly His Gly Ala Thr Phe Thr Ala Asp Lys Ser Met Gly Asn Gly Asp
                245                 250                 255

Gln Gly Glu Asn Gln Lys Pro Met Phe Glu Leu Ala Glu Gly Ala Thr
            260                 265                 270

Leu Lys Asn Val Asn Leu Gly Glu Asn Glu Val Asp Gly Ile His Val
        275                 280                 285

Lys Ala Lys Asn Ala Gln Glu Val Thr Ile Asp Asn Val His Ala Gln
    290                 295                 300

Asn Val Gly Glu Asp Leu Ile Thr Val Lys Gly Glu Gly Gly Ala Ala
305                 310                 315                 320
```

```
Val Thr Asn Leu Asn Ile Lys Asn Ser Ser Ala Lys Gly Ala Asp Asp
            325                 330                 335

Lys Val Val Gln Leu Asn Ala Asn Thr His Leu Lys Ile Asp Asn Phe
        340                 345                 350

Lys Ala Asp Asp Phe Gly Thr Met Val Arg Thr Asn Gly Gly Lys Gln
    355                 360                 365

Phe Asp Asp Met Ser Ile Glu Leu Asn Gly Ile Glu Ala Asn His Gly
370                 375                 380

Lys Phe Ala Leu Val Lys Ser Asp Ser Asp Leu Lys Leu Ala Thr
385                 390                 395                 400

Gly Asn Ile Ala Met Thr Asp Val Lys His Ala Tyr Asp Lys Thr Gln
            405                 410                 415

Ala Ser Thr Gln His Thr Glu Leu
            420

<210> SEQ ID NO 10
<211> LENGTH: 1729
<212> TYPE: DNA
<213> ORGANISM: Pseudomonas syringae

<400> SEQUENCE: 10
```

| | | | | | |
|---|---|---|---|---|---|
| tccacttcgc | tgattttgaa | attggcagat | tcatagaaac | gttcaggtgt | ggaaatcagg | 60 |
| ctgagtgcgc | agatttcgtt | gataagggtg | tggtactggt | cattgttggt | catttcaagg | 120 |
| cctctgagtg | cggtgcggag | caataccagt | cttcctgctg | gcgtgtgcac | actgagtcgc | 180 |
| aggcataggc | atttcagttc | cttgcgttgg | ttgggcatat | aaaaaaagga | acttttaaaa | 240 |
| acagtgcaat | gagatgccgg | caaaacggga | accggtcgct | gcgctttgcc | actcacttcg | 300 |
| agcaagctca | accccaaaca | tccacatccc | tatcgaacgg | acagcgatac | ggccacttgc | 360 |
| tctggtaaac | cctggagctg | gcgtcggtcc | aattgcccac | ttagcgaggt | aacgcagcat | 420 |
| gagcatcggc | atcacacccc | ggccgcaaca | gaccaccacg | ccactcgatt | tttcggcgct | 480 |
| aagcggcaag | agtcctcaac | caaacacgtt | cggcgagcag | aacactcagc | aagcgatcga | 540 |
| cccgagtgca | ctgttgttcg | gcagcgacac | acagaaagac | gtcaacttcg | gcacgcccga | 600 |
| cagcaccgtc | cagaatccgc | aggacgccag | caagcccaac | gacagccagt | ccaacatcgc | 660 |
| taaattgatc | agtgcattga | tcatgtcgtt | gctgcagatg | ctcaccaact | ccaataaaaa | 720 |
| gcaggacacc | aatcaggaac | agcctgatag | ccaggctcct | ttccagaaca | acggcgggct | 780 |
| cggtacaccg | tcggccgata | gcgggggcgg | cggtacaccg | gatgcgacag | gtggcggcgg | 840 |
| cggtgatacg | ccaagcgcaa | caggcggtgg | cggcggtgat | actccgaccg | caacaggcgg | 900 |
| tggcggcagc | ggtggcggcg | gcacacccac | tgcaacaggt | ggcggcagcg | gtggcacacc | 960 |
| cactgcaaca | ggcggtggcg | agggtggcgt | aacaccgcaa | atcactccgc | agttggccaa | 1020 |
| ccctaaccgt | acctcaggta | ctggctcggt | gtcggacacc | gcaggttcta | ccgagcaagc | 1080 |
| cggcaagatc | aatgtggtga | agacaccat | caaggtcggc | gctggcgaag | tctttgacgg | 1140 |
| ccacggcgca | accttcactg | ccgacaaatc | tatgggtaac | ggagaccagg | gcgaaaatca | 1200 |
| gaagcccatg | ttcgagctgg | ctgaaggcgc | tacgttgaag | aatgtgaacc | tgggtgagaa | 1260 |
| cgaggtcgat | ggcatccacg | tgaaagccaa | aaacgctcag | gaagtcacca | ttgacaacgt | 1320 |
| gcatgcccag | aacgtcggtg | aagacctgat | tacggtcaaa | ggcgagggag | cgcagcggt | 1380 |
| cactaatctg | aacatcaaga | acagcagtgc | caaaggtgca | gacgcacaag | gttgtccagct | 1440 |
| caacgccaac | actcacttga | aaatcgacaa | cttcaaggcc | gacgatttcg | gcacgatggt | 1500 |

```
tcgcaccaac ggtggcaagc agtttgatga catgagcatc gagctgaacg gcatcgaagc    1560
taaccacggc aagttcgccc tggtgaaaag cgacagtgac gatctgaagc tggcaacggg    1620
caacatcgcc atgaccgacg tcaaacacgc ctacgataaa acccaggcat cgacccaaca    1680
caccgagctt tgaatccaga caagtagctt gaaaaaaggg ggtggactc                1729
```

<210> SEQ ID NO 11
<211> LENGTH: 344
<212> TYPE: PRT
<213> ORGANISM: Pseudomonas solanacearum

<400> SEQUENCE: 11

```
Met Ser Val Gly Asn Ile Gln Ser Pro Ser Asn Leu Pro Gly Leu Gln
 1               5                  10                  15

Asn Leu Asn Leu Asn Thr Asn Thr Asn Ser Gln Gln Ser Gly Gln Ser
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly Asn Thr Gly
    50                  55                  60

Asn Thr Gly Asn Ala Pro Ala Lys Asp Gly Asn Ala Asn Ala Gly Ala
65                  70                  75                  80

Asn Asp Pro Ser Lys Asn Asp Pro Ser Lys Ser Gln Ala Pro Gln Ser
                85                  90                  95

Ala Asn Lys Thr Gly Asn Val Asp Asp Ala Asn Asn Gln Asp Pro Met
           100                 105                 110

Gln Ala Leu Met Gln Leu Leu Glu Asp Leu Val Lys Leu Leu Lys Ala
       115                 120                 125

Ala Leu His Met Gln Gln Pro Gly Gly Asn Asp Lys Gly Asn Gly Val
   130                 135                 140

Gly Gly Ala Asn Gly Ala Lys Gly Ala Gly Gln Gly Gly Leu Ala
145                 150                 155                 160

Glu Ala Leu Gln Glu Ile Glu Gln Ile Leu Ala Gln Leu Gly Gly Gly
               165                 170                 175

Gly Ala Gly Ala Gly Gly Ala Gly Gly Val Gly Gly Ala Gly Gly
           180                 185                 190

Ala Asp Gly Gly Ser Gly Ala Gly Gly Ala Gly Ala Asn Gly Ala
       195                 200                 205

Asp Gly Gly Asn Gly Val Asn Gly Asn Gln Ala Asn Gly Pro Gln Asn
   210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
               245                 250                 255

Ala Leu Val Gln Met Met Gln Gln Gly Gly Leu Gly Gly Gly Asn Gln
           260                 265                 270

Ala Gln Gly Gly Ser Lys Gly Ala Gly Asn Ala Ser Pro Ala Ser Gly
       275                 280                 285

Ala Asn Pro Gly Ala Asn Gln Pro Gly Ser Ala Asp Asp Gln Ser Ser
   290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
               325                 330                 335

Gln Ser Thr Ser Thr Gln Pro Met
           340
```

-continued

```
<210> SEQ ID NO 12
<211> LENGTH: 1035
<212> TYPE: DNA
<213> ORGANISM: P

15. The method according to claim 1, wherein the postharvest disease is caused by *Penicillium, Botrytis, Phytophthora,* or *Erwinia*.

16. A method of enhancing the longevity of fruit or vegetable ripeness comprising:
   treating a fruit or vegetable with an isolated hypersensitive response elicitor harpin protein or polypeptide derived from a bacterial plant pathogen prior to harvest of the fruit or vegetable, wherein said treating is effective to induce enhanced longevity of ripeness in the treated fruit or vegetable; and
   harvesting the ripeness longevity enhanced fruit or vegetable.

17. The method according to claim 16, wherein hypersensitive response elicitor harpin protein or polypeptide is in isolated form.

18. The method according to claim 16 further comprising repeating said treating after said harvesting.

19. The method according to claim 1, wherein
   the hypersensitive response elicitor harpin protein or polypeptide is selected from the group consisting of SEQ ID NO: 1, 3, 5, 7, 9, 11, and hypersensitive response-eliciting fragments thereof, and
   the fruit or vegetable is selected from the group consisting of citrus, tomato, grape, apple, and lettuce.

20. The method according to claim 16, wherein the hypersensitive response elicitor harpin protein or polypeptide is selected from the group consisting of SEQ ID NO: 1, 3, 5, 7, 9, 11, and hypersensitive response-eliciting fragments thereof.

21. A method of inhibiting postharvest desiccation of a fruit or vegetable, said method comprising:
   treating a fruit or vegetable with an isolated hypersensitive response elicitor harpin protein or polypeptide derived from a bacterial plant pathogen prior to harvest of the fruit or vegetable, wherein said treating is effective to induce postharvest desiccation resistance in the treated fruit or vegetable; and
   harvesting the desiccation resistant fruit or vegetable.

* * * * *

UNITED STATES PATENT AND TRADEMARK OFFICE
CERTIFICATE OF CORRECTION

PATENT NO. : 7,915,217 B2  
APPLICATION NO. : 10/847142  
DATED : March 29, 2011  
INVENTOR(S) : Wei et al.

Page 1 of 1

It is certified that error appears in the above-identified patent and that said Letters Patent is hereby corrected as shown below:

In claim 8, at column 72, lines 48-49, delete "Phytophthora,".

Signed and Sealed this  
Fourteenth Day of June, 2011

David J. Kappos  
*Director of the United States Patent and Trademark Office*